(12) United States Patent
Ikeda et al.

(10) Patent No.: US 12,201,659 B2
(45) Date of Patent: Jan. 21, 2025

(54) FOAMY VIRUSES AND METHODS OF USE

(71) Applicant: Mayo Foundation for Medical Education and Research, Rochester, MN (US)

(72) Inventors: Yasuhiro Ikeda, Rochester, MN (US); Karol M. Budzik, Mount Prospect, IL (US); Stephen James Russell, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1069 days.

(21) Appl. No.: 16/980,359

(22) PCT Filed: Apr. 12, 2019

(86) PCT No.: PCT/US2019/027353
§ 371 (c)(1),
(2) Date: Sep. 11, 2020

(87) PCT Pub. No.: WO2019/209557
PCT Pub. Date: Oct. 31, 2019

(65) Prior Publication Data
US 2021/0046134 A1 Feb. 18, 2021

Related U.S. Application Data

(60) Provisional application No. 62/663,637, filed on Apr. 27, 2018.

(51) Int. Cl.
*A61K 35/768* (2015.01)
*A61P 35/00* (2006.01)
*C12N 7/00* (2006.01)

(52) U.S. Cl.
CPC ............ *A61K 35/768* (2013.01); *A61P 35/00* (2018.01); *C12N 7/00* (2013.01); *C12N 2740/17021* (2013.01); *C12N 2740/17022* (2013.01); *C12N 2740/17032* (2013.01)

(58) Field of Classification Search
None
See application file for complete search history.

(56) References Cited

U.S. PATENT DOCUMENTS

| | | |
|---|---|---|
| 2012/0087894 A1 | 4/2012 | Jolly et al. |
| 2014/0140962 A1 | 5/2014 | Carrico et al. |
| 2016/0083462 A1 | 3/2016 | Yang et al. |
| 2019/0055299 A1 | 2/2019 | Thokala et al. |
| 2019/0085081 A1 | 3/2019 | Bicknell et al. |

FOREIGN PATENT DOCUMENTS

| | | | |
|---|---|---|---|
| EP | 2583974 | 4/2017 | |
| WO | WO 2000/077177 | 12/2000 | |
| WO | WO 2015/142675 | 9/2015 | |
| WO | WO-2018027155 A1 * | 2/2018 | ............ A61K 35/17 |

OTHER PUBLICATIONS

Liu et al. Molecular Ecology and Natural History of Simian Foamy Virus Infection in Wild-Living Chimpanzees. PLoS Pathog. 2008; 4(7): e1000097. p. 1-22. (Year: 2008).*
SFV-1 pol gene restriction analysis. performed on Feb. 20, 2024. (Year: 2024).*
Liu et al., PLoS Pathog. 2008; 4(7): e1000097, p. 1-22. (Year: 2008).*
Meiering et al. Clinical Microbiology Reviews. 2001; 14(1): 165-176. (Year: 2001).*
Bauer et al., Nature Medicine. 2008; 14(1): 93-97. (Year: 2008).*
Beard et al., "Unique Integration Profiles in a Canine Model of Long-Term Repopulating Cells Transduced with Gammaretrovirus, Lentivirus, or Foamy Virus," Hum. Gene Therapy, May 2007, 18(5):423-434.
Budzik et al., "Engineering Simian Foamy Virus for safe and effective tumoricidal therapy," Abstract, Presented at Proceedings of the American Society for Gene and Cell Therapy Conference, Chicago, IL, May 16-19, 2018, No. 758.
Campbell et al., "Characterization of the Internal Promoter of Simian Foamy Viruses," J. Virology, Aug. 1994, 68(8):4811-4820.
Cancer.gov [online], "Cancer Stat Facts: Cancer of Any Site," available on or before Nov. 12, 2015 via Internet Archive: Wayback Machine. URL<https://web.archive.org/web/20051112204314/https://seer.cancer.gov/statfacts/html/all.html>, retrieved Apr. 21, 2021, retrieved from URL<https://seer.cancer.gov/statfacts/html/all.html>, 11 pages.
Chiocca et al., "Oncolytic Viruses and Their Application to Cancer Immunotherapy," Cancer Immunol. Research, Apr. 2014, 2(4):295-300.
Erlwein et al., "Progress and prospects: Foamy virus vectors enter a new age," Gene Therapy, Jul. 15, 2010, 17(12):1423-1429.
GenBank Accession No. L25422.1, "Simian foamy virus type 6 long terminal repeat (LTR)," dated Jun. 5, 1995, 2 pages.
GenBank Accession No. X83297.1, "Simian foamy virus integrase gene (type 7)," dated Jul. 26, 2016, 1 page.
Goodman et al., "Foamy Virus Vector Carries a Strong Insulator in Its Long Terminal Repeat Which Reduces Its Genotoxic Potential," J. Virology, Jan. 2018, 92(1):e01639-17, 25 pages.
Heinkelein et al., "Experimental therapy of allogeneic solid tumors induced in athymic mice with suicide gene-transducing replication-competent foamy virus vectors," Cancer Gene Therapy, Dec. 2005, 12(12):947-953.
Herchenroder et al., "Infectious Proviral Clones of Chimpanzee Foamy Virus (SFVepz) Generated by Long PCR Reveal Close Functional Relatedness to Human Foamy Virus," Virology, Dec. 20, 1995, 214(2):685-689.

(Continued)

*Primary Examiner* — Taeyoon Kim
*Assistant Examiner* — Jianjian Zhu
(74) *Attorney, Agent, or Firm* — Fish & Richardson P.C.

(57) ABSTRACT

This document provides methods and materials for treating cancer. For example, foamy viruses (e.g., simian foamy viruses) are provided as well as methods and materials for treating cancer using foamy viruses as an oncolytic agent.

5 Claims, 28 Drawing Sheets

(56) References Cited

OTHER PUBLICATIONS

Lambert et al., "Potent neutralizing antibodies in humans infected with zoonotic simian foamy viruses target conserved epitopes located in the dimorphic domain of the surface envelope protein," PLoS Pathogens, Oct. 8, 2018, 14(10):e1007293, 26 pages.

Lei et al., "Replication-Competent Foamy Virus Vaccine Vectors as Novel Epitope Scaffolds for Immunotherapy," PLoS One, Sep. 23, 2015, 10(9):e0138458, 27 pages.

Lindemann et al., "Foamy Virus Biology and Its Application for Vector Development," Viruses, May 2011, 3(5):561-585.

Maitra et al., "Reovirus: A Targeted Therapeutic—Progress And Potential," Mol. Cancer Research, Oct. 2012, 10(12):1514-1525.

Mergia et al., "The Efficiency of Simian Foamy Virus Vector Type-1 (SFV-1) in Nondividing Cells and in Human PBLs," Virology, Feb. 15, 2001, 280(2):243-252.

Olszko et al., "Foamy Virus Vectors for HIV Gene Therapy," Viruses, Oct. 22, 2013, 5(10):2585-2600.

PCT International Preliminary Report on Patentability in International Appln. No. PCT/US2019/027353, dated Oct. 27, 2020, 9 pages.

PCT International Search Report and Written Opinion in International Appln. No. PCT/US2019/027353, dated Aug. 12, 2019, 15 pages.

Perez et al., "Design and Selection of Toca 511 for Clinical Use: Modified Retroviral Replicating Vector With Improved Stability and Gene Expression," Mol. Therapy, Sep. 2012, 20(9):1689-1698.

Pesonen et al., "Integrin targeted oncolytic adenoviruses Ad5-D24-RGD and Ad5-RGD-D24-GMCSF for treatment of patients with advanced chemotherapy refractory solid tumors," Int. J. Cancer, Apr. 15, 2012, 130(8):1937-1947.

Pinto-Santini et al., "Foamy virus zoonotic infections," Retrovirology, Dec. 2, 2017, 14(1):55, 14 pages.

Rehman et al., "Into the clinic: talimogene laherparepvec (T-VEC), a first-in-class intratumoral oncolytic viral therapy," J. Immunother. Cancer, Sep. 20, 2016, 4:53, 8 pages.

Rethwilm et al., "Evolution of foamy viruses: the most ancient of all retroviruses," Viruses, Sep. 25, 2013, 5(10):2349-2374.

Richard et al., "Cocirculation of Two env Molecular Variants, of Possible Recombinant Origin, in Gorilla and Chimpanzee Simian Foamy Virus Strains from Central Africa," J. Virology, Dec. 2015, 89(24):12480-12491.

Rua et al., "Genetic Characterization of Simian Foamy Viruses Infecting Humans," J. Virology, Dec. 2012, 86(24):13350-13359.

Rua et al., "Origin, evolution and innate immune control of simian foamy viruses in humans," Curr. Opin. Virology, Feb. 2015, 10:47-55.

Rua et al., "Viral Latency in Blood and Saliva of Simian Foamy Virus-Infected Humans," PLoS One, Oct. 8, 2013, 8(10):e77072, 9 pages.

Russell et al., "Oncolytic Virotherapy: A Contest between Apples and Oranges," Mol. Therapy, May 3, 2017, 25(5):1107-1116.

Russell et al., "Remission of Disseminated Cancer After Systemic Oncolytic Virotherapy," Mayo Clin. Proceedings, Jul. 2014, 89(7):926-933.

Tocagen.com [online], "Our Products: TOCA 511 and TOCA FC," dated Dec. 9, 2019, available on or before Feb. 22, 2016, via Internet Archive: Wayback Machine URL<https://web.archive.org/web/20160222174403/https://tocagen.com/product-candidates/>, retrieved on Apr. 21, 2021, retrieved from URL<https://web.archive.org/web/20191209041027/https://tocagen.com/product-candidates/>, 8 pages.

Budzik et al., "Oncolytic Foamy Virus: Generation and Properties of a Nonpathogenic Replicating Retroviral Vector System That Targets Chronically Proliferating Cancer Cells," J. Virology, Mar. 10, 2021, 95(10):e00015-21, 18 pages.

Galvin et al., "Identification of Recombination in the Envelope Gene of Simian Foamy Virus Serotype 2 Isolated from Macaca cyclopis," J. Virology, Aug. 2013, 87(15):8792-8797.

Hatama et al., "Isolation and sequencing of infectious clones of feline foamy virus and a human/feline foamy virus Env chimera," J. Gen. Virology, Dec. 2001, 82(12):2999-3004.

Jia et al., "Novel microRNA Engineered Oncolytic Virotherapy for Clinical Trial," Abstract, Presented at Proceedings of the American Society for Gene and Cell Therapy Conference, Chicago, IL, May 16-19, 2018, No. 759.

\* cited by examiner

SG - Suicide Gene

- Cancer-specific Promoter
- Suicide Gene

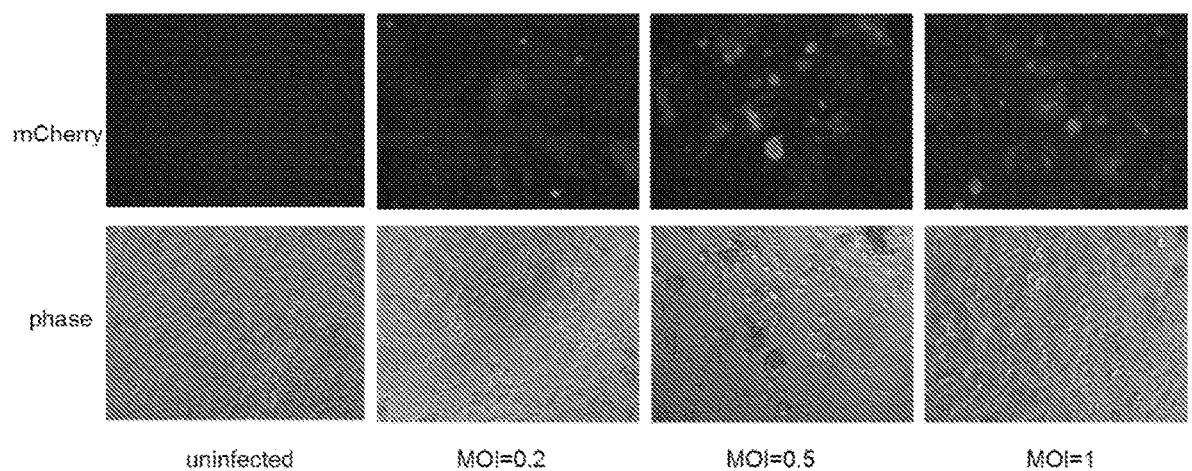
FIG. 12A
FIG. 12B
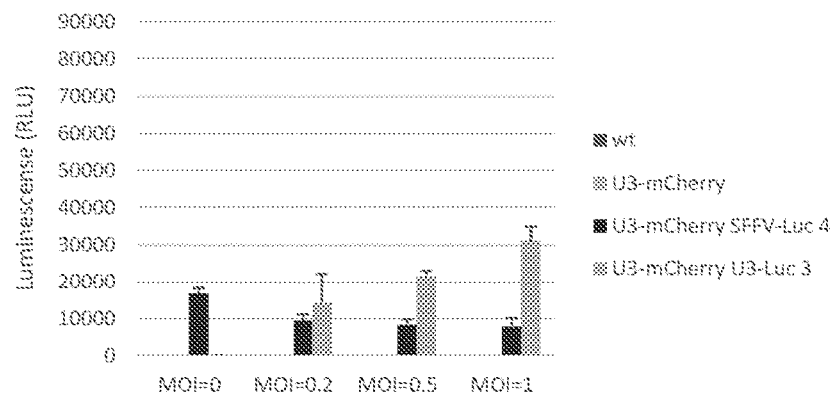
FIG. 12C
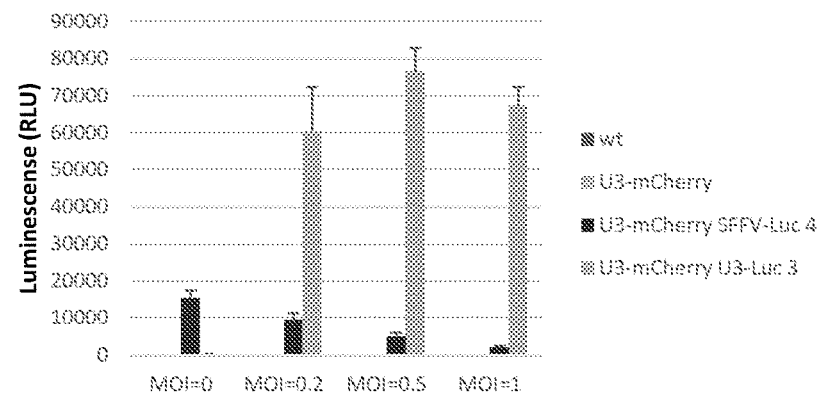

FOAMY VIRUSES AND METHODS OF USE

CROSS-REFERENCE TO RELATED APPLICATIONS

This application is a National Stage application under 35 U.S.C. § 371 of International Application No. PCT/US2019/027353, having an International Filing Date of Apr. 12, 2019, which claims priority to U.S. Application Ser. No. 62/663,637, filed on Apr. 27, 2018. The disclosure of the prior application is considered part of the disclosure of this application, and is incorporated in its entirety into this application.

BACKGROUND

1. Technical Field

This document relates to methods and materials for treating cancer. For example, this document provides methods and materials for treating cancer using recombinant foamy viruses (e.g., recombinant simian foamy viruses (SFVs)) as an oncolytic agent.

2. Background Information

Despite vast efforts, cancer remains a major public health issue in the United States with over 1.6 million new cases in 2017 alone (National Cancer Institute, "Cancer Stat Facts: Cancer of Any Site," seer.cancer.gov/statfacts/html/all.html). Traditional therapies, such as chemotherapeutics, radiation therapy and surgery, often fail, especially when cancer is advanced. One of the reasons is for this that cancer cells can eliminate or modify the components that are targeted by these therapies and effectively avoid being killed. Hence, it is critical to develop therapeutics that becoming resistant to is more difficult.

SUMMARY

Foamy viruses (FVs), also known as Spumaviruses (e.g., a virus in the genus Spumavirus), are retroviruses that infect only dividing cells and induce formation of syncytia—large multinucleated cells. In contrast to its widespread prevalence in various mammalian species, FV infection has not been associated with any diseases in their natural hosts. The natural preference of FVs to infect dividing cells limits the possible off-target infections, whereas the strong cytopathic effect (CPE) caused by the virus can lead to cancer cell death. As described herein, FVs can be used as a retroviral platform for safe oncolytic virotherapy.

This document provides methods and materials for treating cancer. For example, this document provides methods and materials for treating cancer using one or more recombinant FVs (e.g., one or more recombinant SFVs) as an oncolytic agent. In some cases, one or more recombinant FVs can be used to reduce the number of cancer cells (e.g., by infecting and killing cancer cells) in a mammal. In some cases, one or more recombinant FVs can be used to stimulate anti-cancer immune responses in a mammal.

Oncolytic virotherapy can provide an alternative approach to cancer treatment by utilizing selectively replicating viruses to destroy tumors, activate adaptive immune responses and ensure a life-long immunity against the tumors (Russell et al., 2017 *Molecular Therapy* 25:1107-1116). As demonstrated herein, recombinant SFVs that are replication competent and are generated by combining genome segments from chimpanzee SFV types 6 and 7 can be used as anticancer agents to reduce the number of cancer cells within a mammal (e.g., a human).

In general, one aspect of this document features a chimeric SFV including a first genomic fragment of a first SFV strain, and a second genomic fragment of a second SFV strain. The first SFV strain can be a first chimpanzee SFV strain, and the second SFV strain can be a second chimpanzee SFV strain that is different from the first chimpanzee SFV strain. The first SFV strain and the second SFV strain can be serotypically distinct. The first SFV strain can be a chimpanzee PAN1 SFV strain, and the second SFV strain can be a chimpanzee PAN2 SFV strain. The first genomic fragment of the first SFV strain can include a 5' LTR, a nucleic acid encoding a gag polypeptide, and a 5' portion of a nucleic acid encoding pol polypeptide, and the second genomic fragment of the second SFV strain can include a 3' portion of a nucleic acid encoding a pol polypeptide, a nucleic acid encoding a env polypeptide, a nucleic acid encoding a tas polypeptide, a nucleic acid encoding a bel2 polypeptide, and a 3' LTR. The 5' portion of the nucleic acid encoding the pol polypeptide and the 3' portion of the nucleic acid encoding the pol polypeptide can be separated by a SfiI restriction site in the pol polypeptide. The chimeric SFV further also can include a transgene. The transgene can encode a detectable label. The detectable label can be a fluorophore selected from the group consisting of green fluorescent protein, mCherry, yellow fluorescent protein, cyan fluorescent protein, or Tomato. The transgene can encode a suicide polypeptide. The suicide polypeptide can be a thymidine kinase, an inducible Caspase 9, a sodium/iodide symporter, a viral polypeptide, or a nitroreductase. The transgene can encode a receptor. The receptor can be a chimeric antigen receptor (CAR). The CAR can target a cancer antigen. The chimeric SFV further also can include a promoter. The promoter can be substituted for the U3 region of a 3' LTR of the second genomic fragment of the second SFV strain. The promoter can be a cancer-specific promoter (e.g., a promoter from a cancer/testis antigen, a promoter from a carcinoembryonic antigen, a promoter from a melan-A antigen, a promoter from a prostate-specific antigen, or a promoter from a telomerase reverse transcriptase.

In another aspect, this document features methods for treating a mammal having cancer. The methods can include, or consist essentially of, administering, to a mammal, a SFV having oncolytic anti-cancer activity, where the SFV includes a first genomic fragment of a first SFV strain and a second genomic fragment of a second SFV strain different from the first SFV strain. The mammal can be a human. The cancer can be a glioblastoma, a pancreatic adenocarcinoma, a cholangiocarcinoma, a mesothelioma, a melanoma, a prostate cancer, a breast cancer, an ovarian cancer, a liver cancer, or a colorectal cancer. The first SFV strain can be a chimpanzee SFV strain, and the second SFV strain can be a different chimpanzee SFV strain. The first SFV strain and the second SFV strain can be serotypically distinct. The first SFV strain can be a chimpanzee PAN1 SFV strain, and the second SFV strain can be a chimpanzee PAN2 SFV strain. The first genomic fragment of the first SFV strain can include a 5' LTR, a nucleic acid encoding a gag polypeptide, and a 5' portion of a nucleic acid encoding a pol polypeptide, and the second genomic fragment the said second SFV strain can include a 3' portion of a nucleic acid encoding a pol polypeptide, a nucleic acid encoding a env polypeptide, a nucleic acid encoding a tas polypeptide, a nucleic acid encoding a bel2 polypeptide, and a 3' LTR. The 5' portion of the nucleic acid encoding the pol polypeptide and the 3' portion of the nucleic acid encoding the pol polypeptide can be separated by a SfiI restriction site in the nucleic acid encoding the pol polypeptide. The SFV also can include a transgene encoding a suicide polypeptide. The suicide polypeptide can be a thymidine kinase, an inducible Caspase 9, a sodium/iodide symporter, a viral polypeptide, or a nitroreductase. The SFV also can include a promoter. The promoter can be substituted for the U3 region of a 3' LTR of the second genomic fragment of the second SFV strain. The promoter can be a cancer-specific promoter (e.g., a promoter from a cancer/testis antigen, a promoter from a carcinoembryonic antigen, a promoter from a melan-A antigen, a promoter from a prostate-specific antigen, or a promoter from a telomerase reverse transcriptase).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1A contains a PAN1 genome. FIG. 1B contains a PAN2 genome. SfiI is a restriction site that can be used to create a full-length PAN1/PAN2 chimeric genome.

FIG. 2A contains a schematic of an expression construct containing a SFV PAN1 genome. FIG. 2B contains a schematic of an expression construct containing a chimeric SFV PAN1/2c genome. FIG. 2C contains a schematic of an expression construct containing a chimeric SFV PAN1/2c genome encoding GFP.

Figures 3A, 3B:
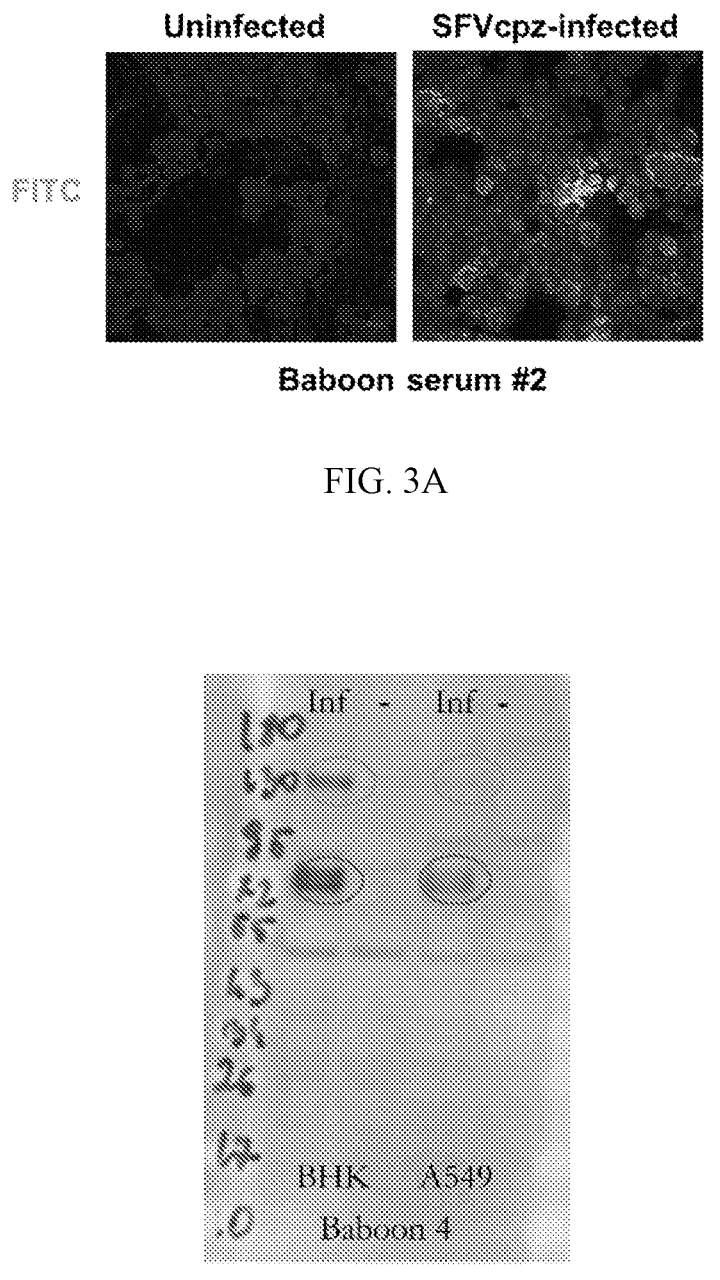

FIGS. 3A and 3B demonstrate detection of SFV proteins by Baboon sera. FIG. 3A contains images of an exemplary indirect fluorescence assay. FIG. 3B contains an exemplary western blot. A549 (for FIGS. 3A and 3B) and BHK-21 (for FIG. 3B) cells were infected with supernatants containing SFVcpz PAN1/2c particles and 4 days later collected for analyses. Samples in FIG. 3A were treated with baboon serum no. 2 and a FITC-conjugated secondary antibody, whereas samples in FIG. 3B were treated with baboon serum no. 4 and a horseradish peroxidase-conjugated secondary antibody. The FITC signal in FIG. 3A indicates detection of SFV antigens. In FIG. 3B, the bands inside the ellipse at 130 kDa indicate the SFV Env protein; the bands inside the ellipse at 73 and 78 kDa indicate the SFV Gag proteins. Inf—infected with SFVcpz; – —not infected cells.

FIG. 5A shows that BHK-21-U3-mCherry cells infected with SFVs express mCherry. FIG. 5B shows that BHK-21-U3-GFP cells infected with SFVs express GFP.

Figure 6:
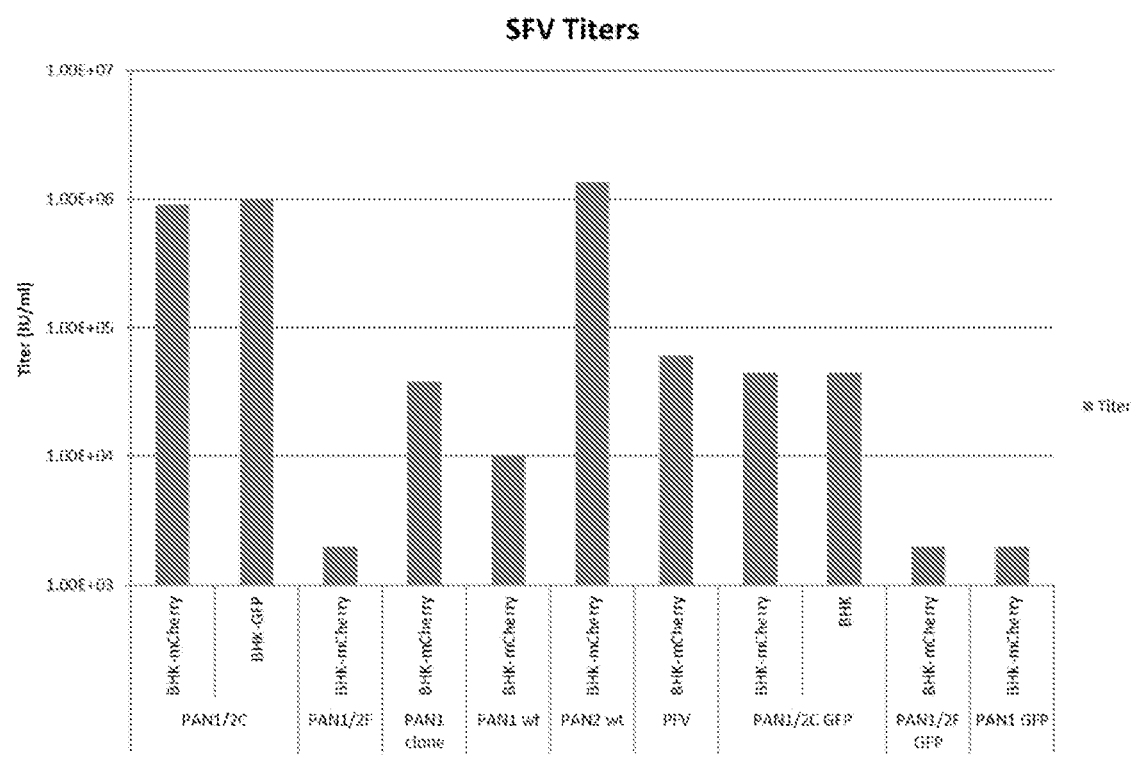

FIG. 6 contains a graph showing titers of the SFVs used in the study, as determined using the BHK indicator cells. Virus name and type of the cells used for determination is indicated under each bar.

FIG. 7A shows U251 glioblastoma cells infected with SFVs and PFV. FIG. 7B shows Mia Paca pancreatic adenocarcinoma cells infected with SFVs and PFV. FIG. 7C shows CDB-1 cholangiocarcinoma cells infected with SFVs and PFV.

FIG. 9A contains a SFVcpz genome with the U3 region of the 3' LTR replaced with a cancer-specific promoter. FIG. 9B contains a SFVcpz genome with the U3 region of the 3' LTR replaced with a cancer-specific promoter and the nucleic acid encoding the tas polypeptide deleted.

FIG. 10A contains a SFVcpz genome with the nucleic acid encoding the bel2 polypeptide replaced with a nucleic acid encoding a suicide polypeptide. FIG. 10B contains a SFVcpz genome with the nucleic acid encoding the bel2 polypeptide replaced with a nucleic acid encoding suicide polypeptide and the U3 region of the 3' LTR replaced with a cancer-specific promoter.

FIG. 11A contains a multistep growth curve in the indicator BHK-21-U3-mCherry cells. The cells were infected with the indicated viruses at MOI=0.01 and were sampled every other day for Flow Cytometry analysis to determine the percentage of mCherry (or GFP) positive cells. FIG. 11B contains a graph of titers of the cell-free and cell-associated progeny viruses on day 8 of the experiment described in FIG. 11A. FIG. 11C contains a one-step growth curve in BHK-21-U3-mCherry cells. The cells were infected with PAN1/2 or PAN1/2-GFP at MOI=3 and the supernatants were collected at the indicated time points to measure the viral titers.

FIGS. 12A-12E show indicator U251-U3-mCherry-luciferase cells. FIG. 12A contains a graph showing that the indicator cells were infected at indicated MOIs and imaged 3 days post infection. The number of mCherry-expressing cells increases with the MOI. FIGS. 12B and 12C contain graphs showing luminescence of U251-U3-mCherry-luciferase, Wildtype (wt) U251 and U251-U3-mCherry and U251-U3-mCherry-SFFV-luciferase cells that were infected at the indicated MOIs and bioluminescence after luciferin addition was measured on day 3 (FIG. 12B) and day 4 (FIG. 12C). U251 and U251-U3-mCherry cells do not express luciferase in response to FV infection. U251-U3-mCherry-SFFV-Luc cells express luciferase regardless of FV infection. The expression of luciferase by infected U251-U3-mCherry-luciferase cells increases over time. FIG. 12D contains a graph showing the percent of indicator cells that express mCherry in response to FV infection and the number of mCherry positive cells increases over time. FIG. 12E shows that the replication of FV can be imaged in tumors formed by U251-U3-mCherry-luciferase cells by bioluminescence imaging with the Xenogen system. The image was taken 4 days post injection.

FIG. 13A contains graphs showing tumor bearing mice injected with PBS (mice #1-5), PAN1/2 (mice #6-15), and PFV (mice #16-25) were weighed twice a week. No toxicity was observed after FV injection. FIG. 13B shows that tumors injected with PAN1/2 and PFV display bioluminescence. The mice were imaged once a week after an intraperitoneal injection of luciferin. Three distinct time points are shown here: 12, 49, and 86 days after the first injection. The number of mice imaged decreased over time as the mice were sacrificed (both planned euthanasia for the virus spread analysis and euthanasia due to tumor burden). FIG. 13C shows tumor volume over time per animal for the PBS, PAN1/2 and PFV-injected groups.

FIG. 14A shows infection of FV-injected tumors harvested at 3 time points: day 7, day 34 and day 62 post $1^{st}$ virus injection. The tumor cells were analyzed by flow cytometry to determine the percentage of mCherry positive cells. PBS-injected tumors (the second and the third time point) or uninfected U251-U3-mCherry-luciferase cells (the first time point) were used as the negative control. The shift in the fluorescence intensity in relation to the negative control indicates a substantial increase in the number of mCherry positive (infected) cells. FIG. 14B contains immunohistochemistry images showing mCherry positive cells in the PAN1/2-injected tumor, and the lack of mCherry positive cells in the PBS-injected tumors. Tumors were harvested 62 days after the first virus injection.

FIG. 15A shows the weight of tumor bearing mice injected with PAN1/2-GFP that were weighed twice a week. The mice did not show any toxicity after virus injection. FIG. 15B shows tumors infected with PAN1/2-GFP display bioluminescence after IP luciferin injection. The mice were imaged once a week. Three time points are shown here (day 12, 35 and 56 after infection). The number of mice imaged decreased over time due to planned euthanasia for the virus spread analysis. FIG. 15C shows tumor growth over time per animal. FIG. 15D contains immunohistochemistry images of PBS and PAN1/2-GFP injected tumors stained for mCherry and GFP. PAN1/2-GFP injected tumors are positive for mCherry and GFP. PBS-injected tumors are negative for both fluorophores. Tumors used for immunostaining were harvested 39 and 66 days after infection.

FIG. 16A contains a western blot of lysates of uninfected BHK-21 cells, BHK-21 cells infected with PAN1/2-GFP or PAN1/2-TK that were analyzed for TK expression. 40 kDa protein indicating Thymidine Kinase was detected only in the lysates of the cells infected with PAN1/2-TK. FIG. 16B contains a multistep growth curve of PAN1/2, PAN1/2-GFP and PAN1/2-TK in BHK-21-U3-mCherry cells. FIG. 16C shows U251-U3-mCherry cells infected with PAN1/2-TK and treated with Ganciclovir show a lower number of viable mCherry expressing cells than cells treated with a mock control, infected with PAN1/2 or uninfected. FIG. 16D shows viability of U251-U3-mCherry cells infected with PAN1/2-TK, PAN1/2-GFP (MOI=1) or not infected, and treated with GCV (20 µM). The results are presented as percent of viability of a DMSO-treated control. Asterisk marks statistically significant reduction of viability. ns—not statistically significant reduction of viability. FIG. 16E shows viability of CT-26-U3-mCherry cells infected with PAN1/2-TK, PAN1/2-GFP (MOI=1) or not infected, and treated with GCV (20 µM). The results are presented as percent of viability of a DMSO-treated control.

FIG. 17A shows IFNβ induction by viral infection. A549 cells were infected with VSV, FV (PAN1) or Mengovirus at indicated MOIs. Interferon β production was measured in the supernatants of the infected cells by ELISA 24 and 48 hours post infection and the final result is shown as absorbance measured at 450 nm wavelength. FIG. 18B shows that IFNβ pre-treatment reduced successful infection with PAN1/2-GFP. Patient-derived GBM22 cells were treated with IFNβ or left untreated, then treated with Ruxolitinib or DMSO control. Subsequently, the cells were infected with PAN1/2-GFP. The cells were imaged 6 days post infection. FIG. 17C shows that pre-treatment with IFNβ significantly decreased the titers of PAN1/2-GFP produced by the infected GBM22 cells. The titers were measured 6 days post infection. Asterisk marks statistically significant reduction of viral titers.

DETAILED DESCRIPTION

Figure 1A:
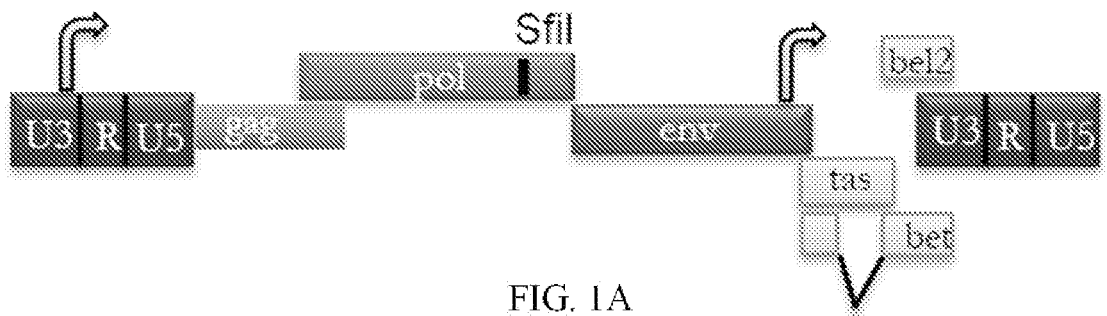
FIGS. 1A and 1B contain exemplary structures of post-reverse transcription SFV genomes.

This document provides methods and materials for treating cancer. For example, this document provides methods and materials for treating cancer using one or more recombinant FVs as an oncolytic agent. In some cases, this document provides recombinant FVs (e.g., recombinant SFVs) having oncolytic anti-cancer activity. In some cases, this document provides methods for using one or more recombinant FVs provided herein to treat a mammal having, or at risk of having, cancer. For example, one or more recombinant FVs can be administered to a mammal having, or at risk of having, cancer to reduce the number of cancer cells (e.g., by infecting and killing cancer cells) in the mammal (e.g., a human). For example, one or more recombinant FVs can be administered to a mammal having, or at risk of having, cancer to stimulate anti-cancer immune responses in the mammal (e.g., a human).

In some cases, a recombinant FV described herein (e.g., a recombinant FV having oncolytic anti-cancer activity) can be replication competent.

In some cases, a recombinant FV described herein (e.g., a recombinant FV having oncolytic anti-cancer activity) are non-pathogenic (e.g., to a mammal being treated as described herein).

In some cases, a recombinant FV described herein (e.g., a recombinant FV having oncolytic anti-cancer activity) can infect dividing cells (e.g., can infect only dividing cells).

In some cases, a recombinant FV described herein (e.g., a recombinant FV having oncolytic anti-cancer activity) can bud through the endoplasmic reticulum.

In some cases, a recombinant FV described herein (e.g., a recombinant FV having oncolytic anti-cancer activity) can bind to a cellular receptor (e.g., to facilitate viral entry to a cell). For example, a recombinant FV described herein can bind to a heparan sulfate cellular receptor.

Recombinant FVs described herein (e.g., recombinant FVs having oncolytic anti-cancer activity) can include one or more nucleotide sequences that do not naturally occur in that FV (e.g., do no naturally occur in that FV prior to recombination). Nucleotide sequences that do not naturally occur in the FV can be from any appropriate source. In some cases, a nucleotide sequence that does not naturally occur in that FV can be from a non-viral organism. In some cases, a nucleotide sequence that does not naturally occur in that FV can be from a virus other than a FV In some cases, a nucleotide sequence that does not naturally occur in that FV can be from a FV obtained from a different species. In some cases, a nucleotide sequence that does not naturally occur in that FV can be from a different strain of FV (e.g., serotypically distinct strains). In some cases, a nucleotide sequence that does not naturally occur in that FV can be a synthetic nucleotide sequence.

Recombinant FVs described herein (e.g., recombinant FVs having oncolytic anti-cancer activity) can be derived from (e.g., can include genomic elements such as nucleic acids encoding a polypeptide (or fragments thereof)) from any appropriate FV. FVs can be isolated from any appropriate species. For example, FVs can be isolated from non-human primates (e.g., monkeys such as Old World monkey species), humans, cats, cows, horses, or bats. In some cases, a recombinant FV can include one or more nucleic acids encoding a polypeptide (or fragments thereof) from a simian FV (SFV). Examples of simian species from which SFVs can be obtained include, without limitation, chimpanzee, gorilla, orangutan, African green monkey, baboon, macaque, marmoset, gibbon ape, cynomolgus monkey, and squirrel monkey. For example, a recombinant FV described herein can include one or more nucleic acids encoding a polypeptide (or fragments thereof) and/or one or more viral elements from a SFV genome obtained from a chimpanzee (e.g., a chimpanzee SFV such as a type 6 (PAN1) SFV strain and/or a type 7 (PAN2) SFV strain). In some cases, a recombinant FV can include one or more nucleic acids encoding a polypeptide (or fragments thereof) and/or one or more viral elements from a FV be obtained from a human (e.g., a human foamy virus (HFV) and a prototype foamy virus (PFV)).

Figure 1B:
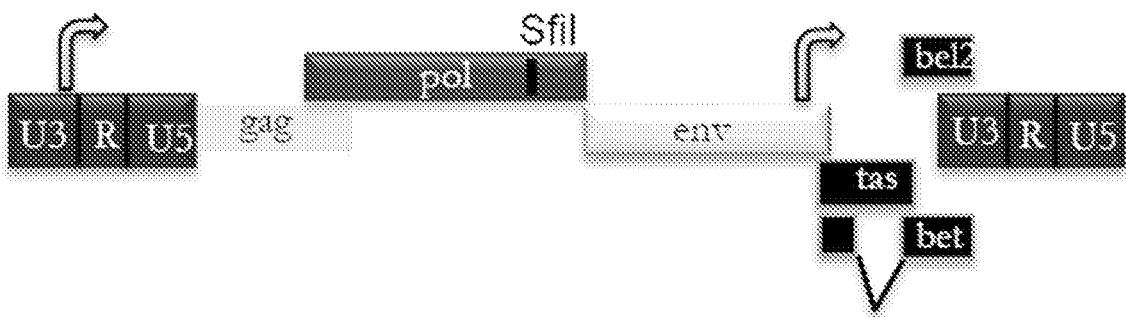

Nucleic acids that can be included in a FV genome include, for example, gag nucleic acid (e.g., nucleic acid encoding the group-specific antigen protein), polynucleic acid (e.g., nucleic acid encoding the DNA polymerase), env nucleic acid (e.g., nucleic acid encoding the envelope protein), tas nucleic acid (e.g., nucleic acid encoding the transactivator protein), and bel2 nucleic acid (e.g., nucleic acid encoding the Bet protein). Viral elements that can be included in a FV genome include, without limitation, a 5' long terminal repeat (LTR) and a 3' LTR, each of which can include a U3 region, a R region, and a U5 region. An exemplary schematic FV genome is shown in FIG. 1.

Figure 2A:
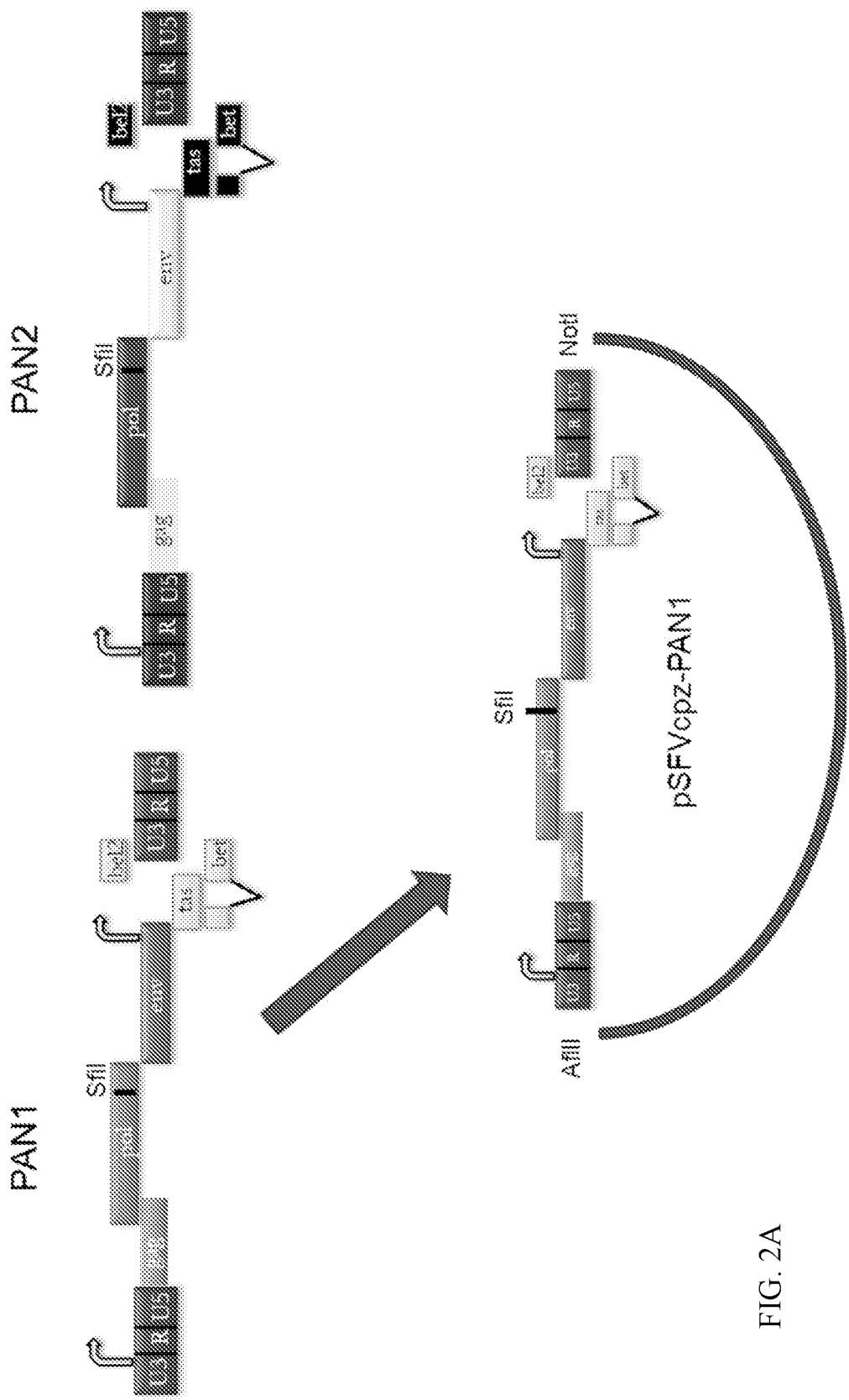
FIGS. 2A-2C contain exemplary genetic structures of the constructed infectious recombinant SFV clones.
Figure 2B:
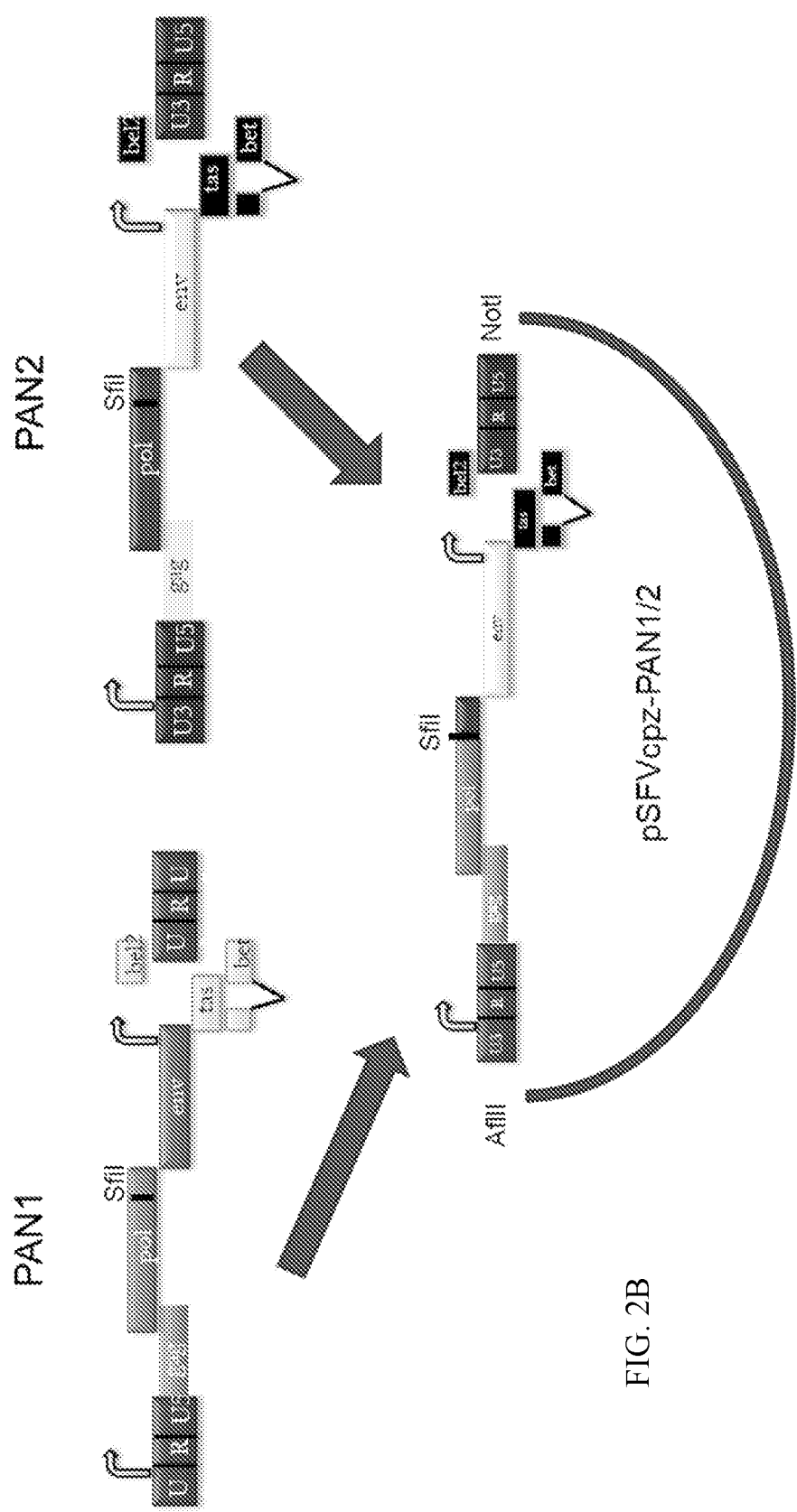

In some cases, a recombinant FV (e.g., SFV) described herein (e.g., a recombinant FV having oncolytic anti-cancer activity) can include a chimeric FV genome. A chimeric FV genome can include one or more nucleic acids encoding a polypeptide (or fragments thereof) and/or one or more viral elements from two or more (e.g., two, three, four, five, or more) different FV genomes. For example, a recombinant FV (e.g., SFV) described herein can include one or more nucleic acids encoding a polypeptide (or fragments thereof) and/or one or more viral elements from two or more different strains of FV isolated from the same species. In some cases, a recombinant SFV described herein can include one or more nucleic acids encoding a polypeptide (or fragments thereof) and/or one or more viral elements from a PAN1 strain of a chimpanzee SFV and one or more nucleic acids encoding a polypeptide (or fragments thereof) and/or one or more viral elements from a PAN2 strain of a chimpanzee SFV. A PAN1 or PAN2 strain of SFV can have a sequence set forth in, for example, National Center for Biotechnology Information (NCBI) Accession Nos: L25422 (for PAN1) and X83297 (for PAN2). In some cases, a recombinant SFV having oncolytic anti-cancer activity can include the 5' LTR, the gag nucleic acid, and a portion (e.g., a first portion such as the 5' portion) of the pol nucleic acid from a PAN1 SFV and a portion (e.g., a second portion such as the 3' portion) of the pol nucleic acid, the env nucleic acid, the tas nucleic acid, the bel2 nucleic acid, and the 3' LTR from a PAN2 SFV. For example, a recombinant SFV having oncolytic anti-cancer activity can include from the 5' LTR to the SfiI restriction site (localized in the pol nucleic acid) from a PAN1 SFV and from the SfiI restriction site (localized in the pol nucleic acid) to the 3' LTR from a PAN2 SFV (see, e.g., FIG. 2B).

In some cases, a recombinant FV (e.g., SFV) described herein (e.g., recombinant FVs having oncolytic anti-cancer activity) can include one or more nucleic acids encoding a polypeptide (or fragments thereof) and/or one or more viral elements from two or more FVs isolated from different species (e.g., one or more nucleic acids encoding a polypeptide (or fragments thereof) and/or one or more viral elements from a chimpanzee SFV and one or more nucleic acids encoding a polypeptide (or fragments thereof) and/or one or more viral elements from a human FV such as PVF).

In some cases, a recombinant FV (e.g., SFV) described herein (e.g., a recombinant FV having oncolytic anti-cancer activity) can include a FV genome containing one or more modifications to one or more nucleic acids encoding a polypeptide (or fragments thereof) and/or one or more viral elements of the FV genome. The one or more modifications can be any appropriate modification. Examples of modifications that can be made to a nucleic acid encoding a polypeptide or to a viral element include, without limitation, deletions, insertions, and substitutions. For example, a recombinant FV can include one or more genomic deletions. In some cases, a recombinant FV can have a deletion (e.g., a full deletion or a partial deletion) of the bel2 nucleic acid. In some cases, a recombinant FV can have a deletion (e.g., a full deletion or a partial deletion) of the tas nucleic acid. In some cases, a recombinant FV can have a deletion (e.g., a full deletion or a partial deletion) of the U3 region of the 3' LTR. For example, a recombinant FV can include one or more genomic insertions (e.g., insertion of one or more transgenes). In some cases, a recombinant FV can include a transgene (e.g., a nucleic acid encoding a suicide polypeptide). In some cases, a recombinant FV can include a regulatory element (e.g., promoter such as a cancer-specific promoter). For example, a recombinant FV can include one or more genomic substitutions (e.g., a substitution of one or more nucleic acids encoding a polypeptide with one or more transgenes). In some cases, a recombinant FV can have a U3 region of the 3' LTR substituted with a cancer-specific promoter. In some cases, a recombinant FV can have bel2 nucleic acid replaced with a transgene (e.g., a nucleic acid encoding a suicide polypeptide).

In cases where a recombinant FV described herein (e.g., a recombinant FV having oncolytic anti-cancer activity) includes a transgene, the transgene can be any appropriate transgene. In some cases, a transgene can be a nucleotide sequence encoding a detectable label. Examples of detectable labels include, without limitation, fluorophores (e.g., green fluorescent protein (GFP), mCherry, yellow fluorescent protein (YFP), cyan fluorescent protein (CFP), and Tomato), enzymes (e.g., luciferase, CRISPR associated protein 9 (Cas9), Cre recombinase, restriction enzymes, convertases, thymidine kinases, and sodium/iodide symporters (NISs)), and antigens.

In some cases, a transgene can be a nucleotide sequence encoding a receptor (e.g., a chimeric antigen receptor (CAR)). A receptor, such as a CAR, can target any appropriate antigen (e.g., a cancer antigen). Examples of antigens that can be targeted by a receptor encoded by a transgene in a recombinant FV described herein include, without limitation, HER2, CA125, CD19, CD30, CD33, CD123, FLT3, BCMA, carcinoembryonic antigen (CEA), melan-A antigen, prostate-specific antigen (PSA), IL13Rα2, epidermal growth factor receptor (EGFR), EGFRvIII, mesothelin, epithelial cell adhesion molecule (EpCam), thyroid stimulating hormone receptor (TSHR), CD171, CS-1, CD-2 subset 1, CRACC, SLAMF7, CD319, 19A24, C-type lectin-like molecule-1 (CLL-1), ganglioside GD3, Tn antigen (Tn Ag), fms-like tyrosine kinase 3 (FLT3), CD38, CD44v6, B7H3 (CD276), KIT (CD117), interleukin-13 receptor subunit alpha-2 (IL-13Ra2), interleukin 11 receptor alpha (IL-11Ra), prostate stem cell antigen (PSCA), protease serine 21 (PRSS21), vascular endothelial growth factor receptor 2 (VEGFR2), Lewis(Y) antigen, CD24, platelet-derived growth factor receptor beta (PDGFR-beta), stage-specific embryonic antigen-4 (SSEA-4), mucin 1, cell surface associated (MUC1), neural cell adhesion molecule (NCAM), carbonic anhydrase IX (CAIX), proteasome (prosome, macropain) subunit beta type 9 (LMP2), ephrin type-A receptor 2 (EphA2), fucosyl GM1, sialyl Lewis adhesion molecule (sLe), ganglioside GM3, TGS5, high molecular weight-melanoma-associated antigen (HMWMAA), o-acetyl-GD2 ganglioside (OAcGD2), folate receptor beta; tumor endothelial marker 1 (TEM1/CD248), tumor endothelial marker 7-related (TEM7R), claudin 6 (CLDN6), G protein-coupled receptor class C group 5 member D (GPRC5D), chromosome X open reading frame 61 (CXORF61), CD97, CD179a, anaplastic lymphoma kinase (ALK), polysialic acid, placenta-specific 1 (PLAC1), hexasaccharide portion of globoH glycoceramide (GoboH), mammary gland differentiation antigen (NY-BR-1), uroplakin 2 (UPK2), hepatitis A virus cellular receptor 1 (HAVCRI), adrenoceptor beta 3 (ADRB3), pannexin 3 (PANX3); G protein-coupled receptor 20 (GPR20), lymphocyte antigen 6 complex locus K (LY6K), olfactory receptor 51E2 (OR51E2), TCR gamma alternate reading frame protein (TARP), Wilms tumor protein (WTi), ETS translocation-variant gene 6 located on chromosome 12p (ETV6-AML), sperm protein 17 (SPA17), X antigen family member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, p53 mutant, human telomerase reverse transcriptase (hTERT), sarcoma translocation breakpoints, melanoma inhibitor of apoptosis (ML-IAP), ERG—transmembrane protease serine 2 (TMPRSS2) fusion; N-acetyl glucosaminyl-transferase V (NA17), paired box protein Pax-3 (PAX3), androgen receptor; cyclin B1, v-myc avian myelocytomatosis viral oncogene neuroblastoma derived homolog (MYCN), Ras homolog family member C (RhoC), Ccytochrome P450 1B1 (CYP1B1), CCCTC-binding factor (zinc finger protein)-Like (BORIS), squamous cell carcinoma antigen recognized by T cells 3 (SART3), paired box protein Pax-5 (PAX5), proacrosin binding protein sp32 (OY-TES 1), lymphocyte-specific protein tyrosine kinase (LCK), A kinase anchor protein 4 (AKAP-4), synovial sarcoma, X breakpoint 2 (SSX2), CD79a, CD79b, CD72, leukocyte-associated immunoglobulin-like receptor 1 (LAIR1), Fc fragment of IgA receptor (FCAR), leukocyte immunoglobulin-like receptor subfamily A member 2 (LILRA2), CD300 molecule-like family member F (CD300LF), C-type lectin domain family 12 member A (CLECI2A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRL5), and immunoglobulin lambda-like polypeptide 1 (IGLL1).

In cases where a transgene is a nucleotide sequence encoding a CAR, the CAR can be any appropriate type of CAR. For example, a CAR can be a first, second, third, or fourth generation CAR. In some cases, a CAR can include an extracellular domain (e.g., which can interact with a target molecule such as an antigen), a transmembrane domain, and an intracellular domain. In some cases, an extracellular domain of a CAR can include an antigen recognition region that can bind the target antigen, a signal peptide, and, optionally, a spacer/linker. In some cases, an extracellular domain of a CAR can include a single-chain variable fragment (scFv) including the light (VL) and heavy (VH) chains of an immunoglobin (e.g., an immunoglobulin that can bind the target antigen). In some cases, a transmembrane domain of a CAR can include a hydrophobic alpha helix that spans a cell membrane. For example, a transmembrane domain of a CAR can be a CD28 transmembrane domain. For example, a transmembrane domain of a CAR can be a CD3-zeta transmembrane domain. In some cases, an intracellular domain of a CAR can include a cytoplasmic end of a receptor that can, when a target antigen is bound to the extracellular domain of the CAR, activate T cell signaling of a T cell presenting the CAR. An intracellular domain of a CAR can be a recombinant cytoplasmic domain. An intracellular domain of a CAR can be a chimeric cytoplasmic domain. Examples of domains that can be used as a cytoplasmic domain of an intracellular domain of a CAR include, without limitation, a CD3-zeta cytoplasmic domain, a CD28 domain, a 4-1BB (CD127) domain, and an OX40 domain. In some cases, a CAR can be as described in, for example, International Patent Publication No. WO 2015/142675 (see, e.g., paragraph [0243], paragraph [0269], and FIG. 59A), US Patent Publication No. 2019/085081 (see, e.g., paragraphs [0298]-[0308]), and US Patent Publication No. 2019/055299 (see, e.g., paragraphs [0061], [0064]-[0099]).

Figure 2C:
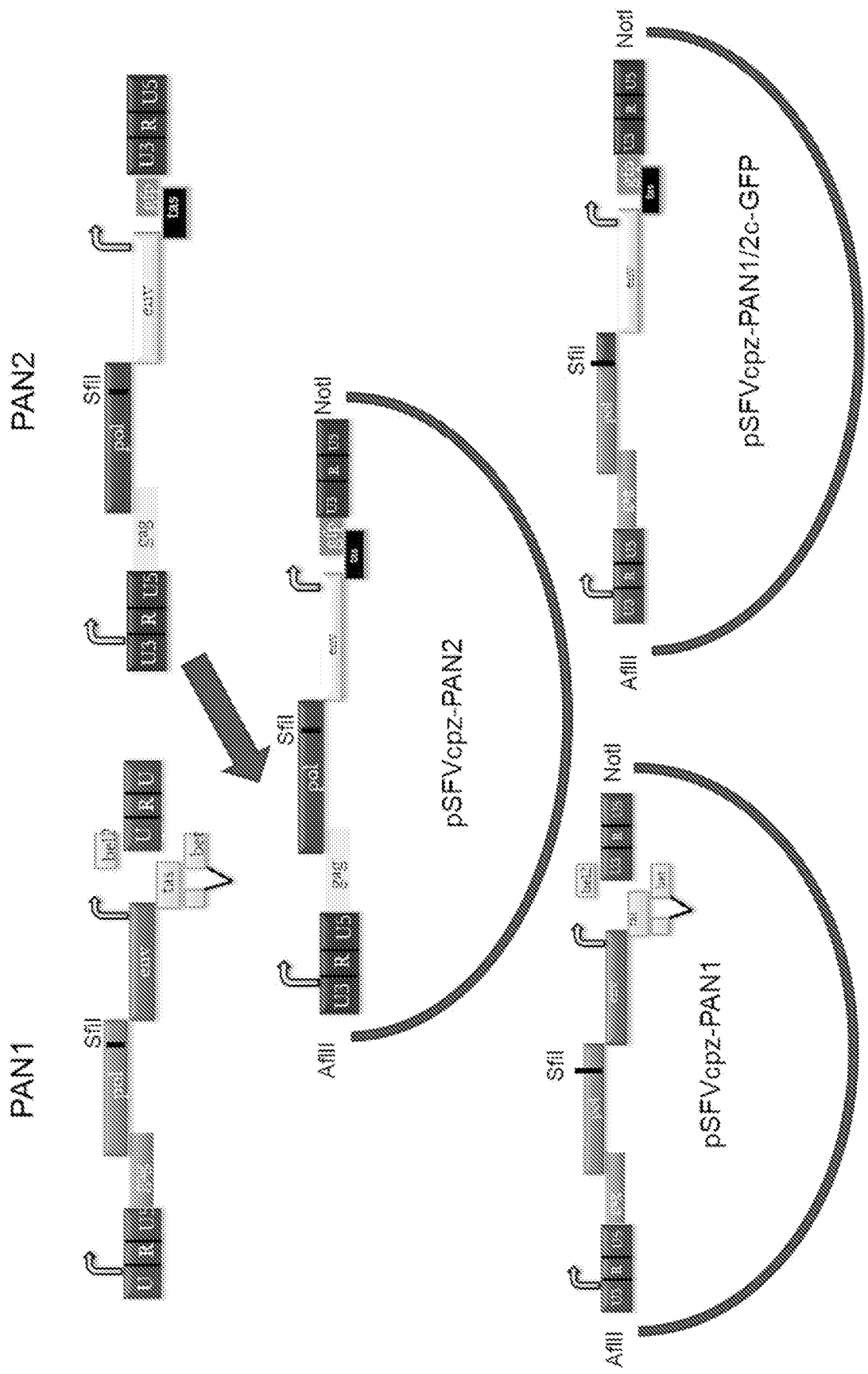
Figure 4:
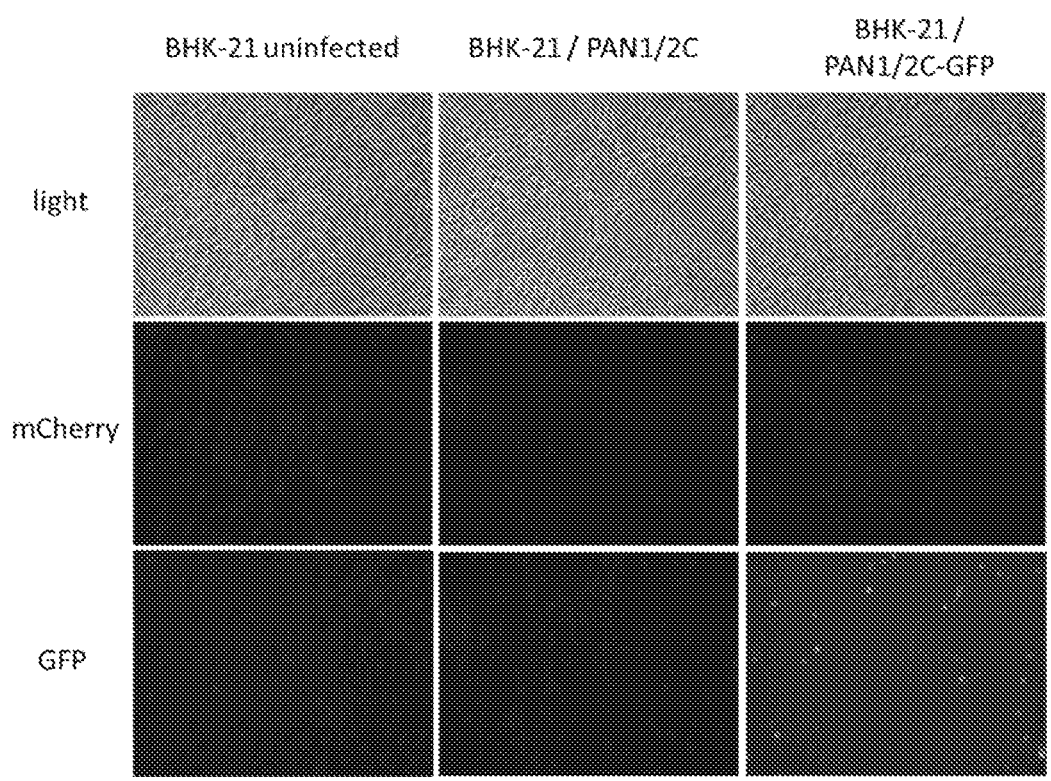
FIG. 4 contains light microscopy images showing that BHK-21 cells infected with PAN1/2c lack mCherry expression.
Figure 5A:
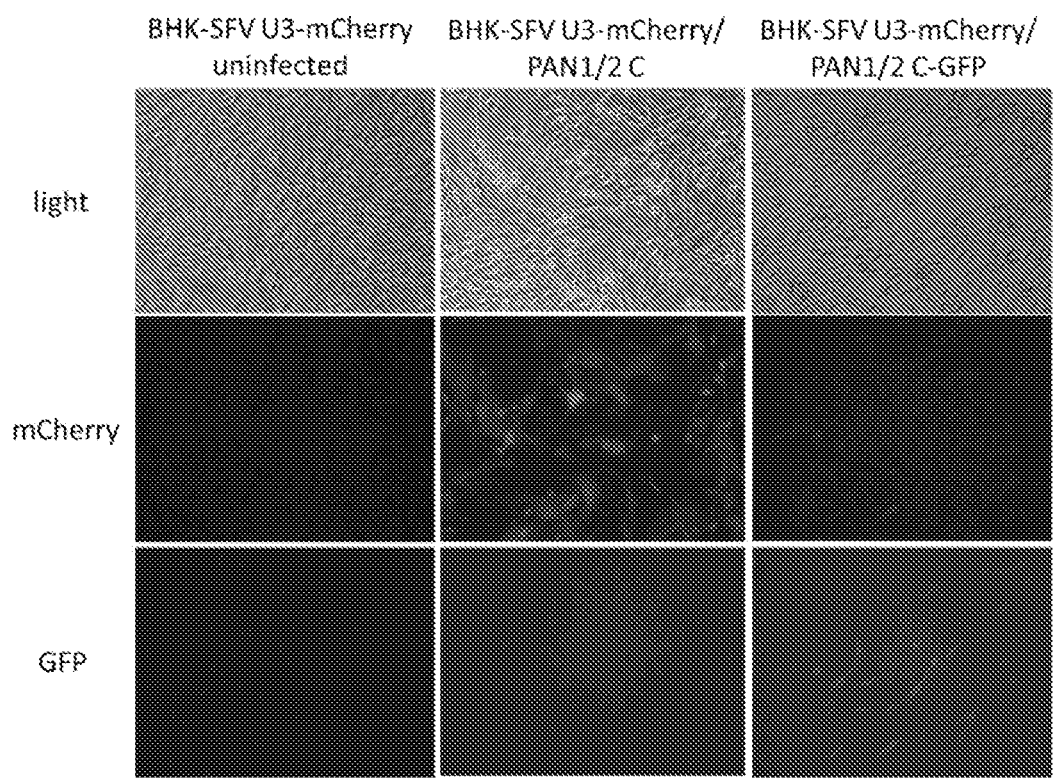
FIGS. 5A and 5B contain light microscopy images showing indicator lines infected with recombinant SFVs.
Figure 5B:
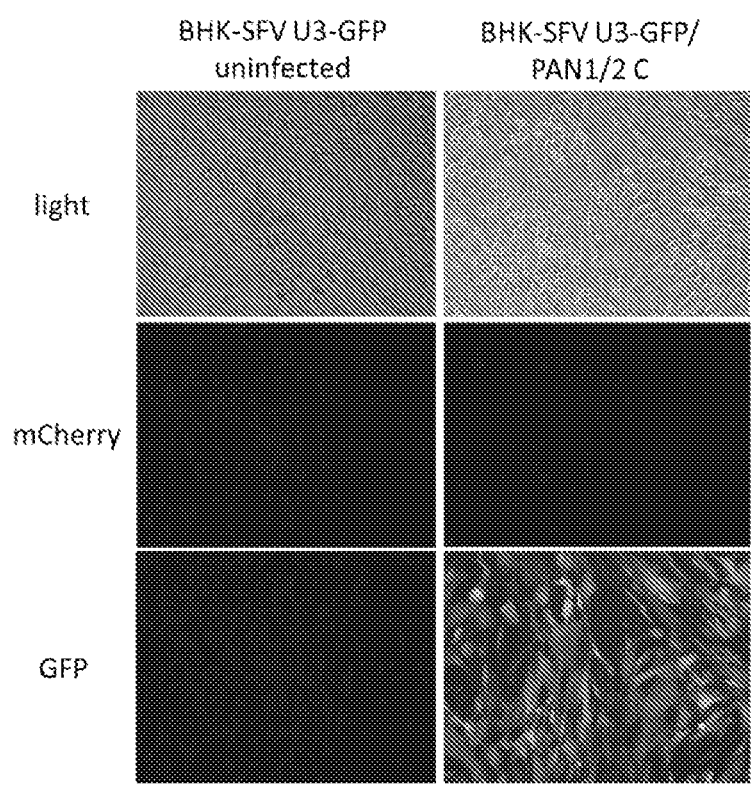
Figure 7A:
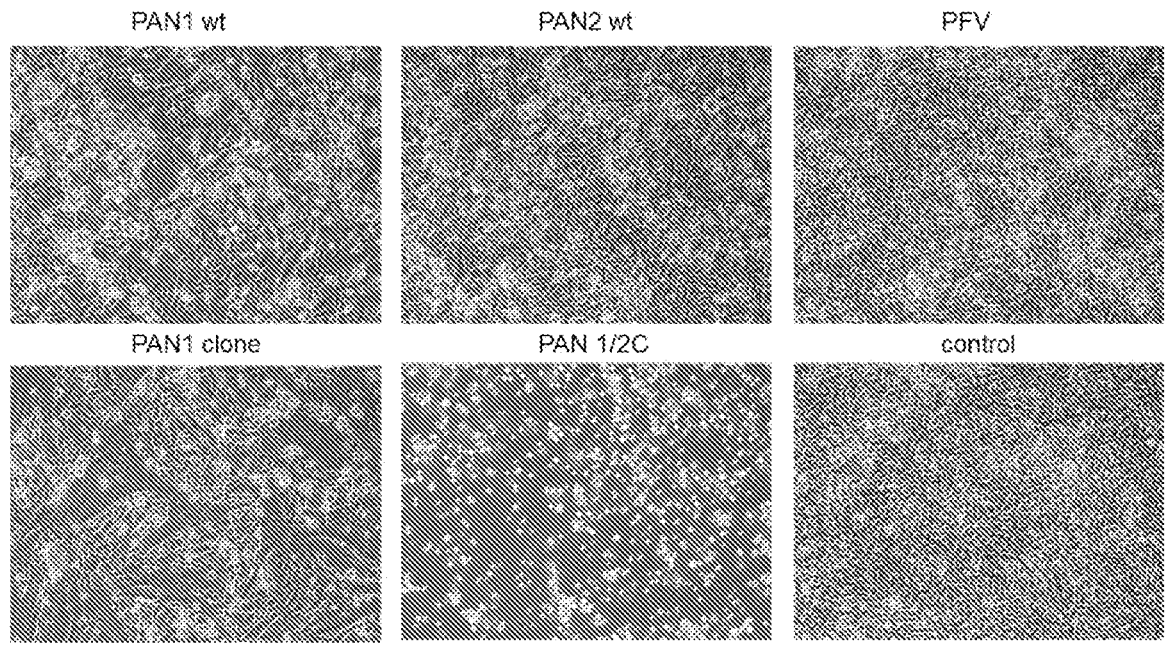
FIGS. 7A-7C contain light microscopy images showing that SFVs and prototype foamy virus (PFV) show different cytotoxicity in cancer cell lines.
Figure 7B:
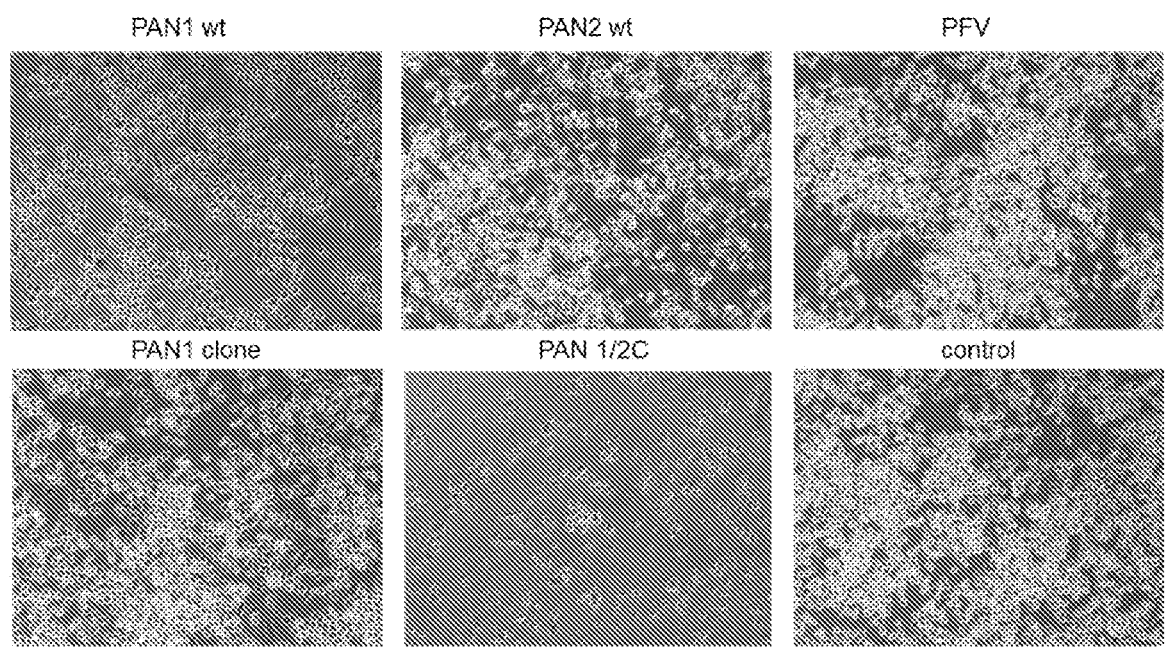
Figure 7C:
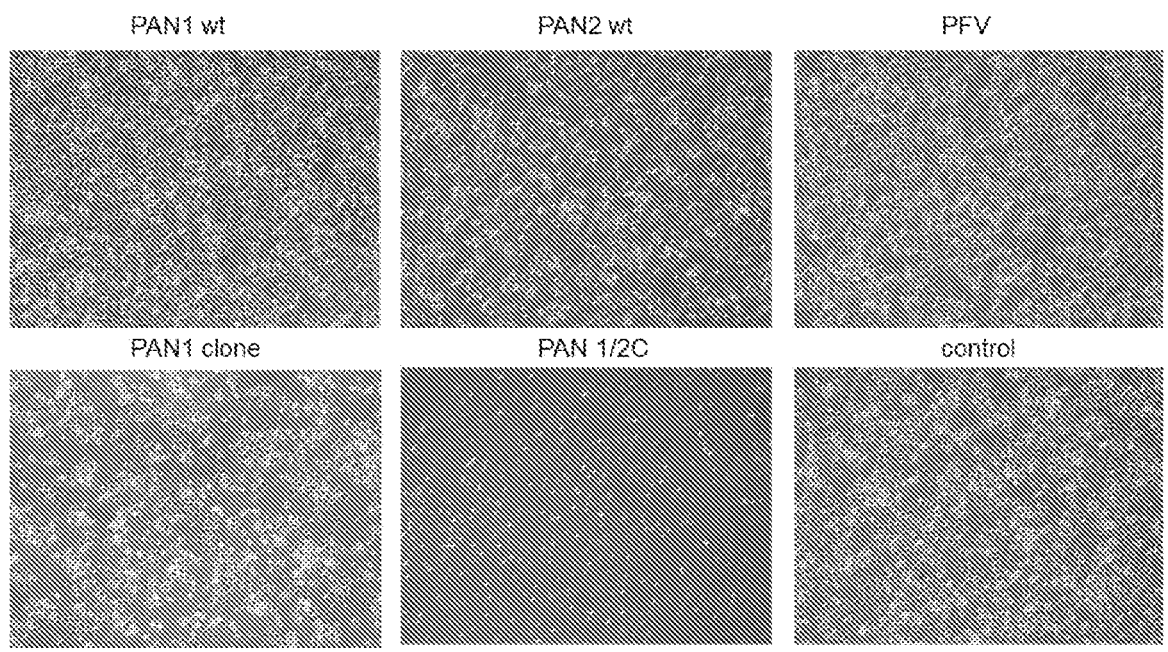
Figure 8:
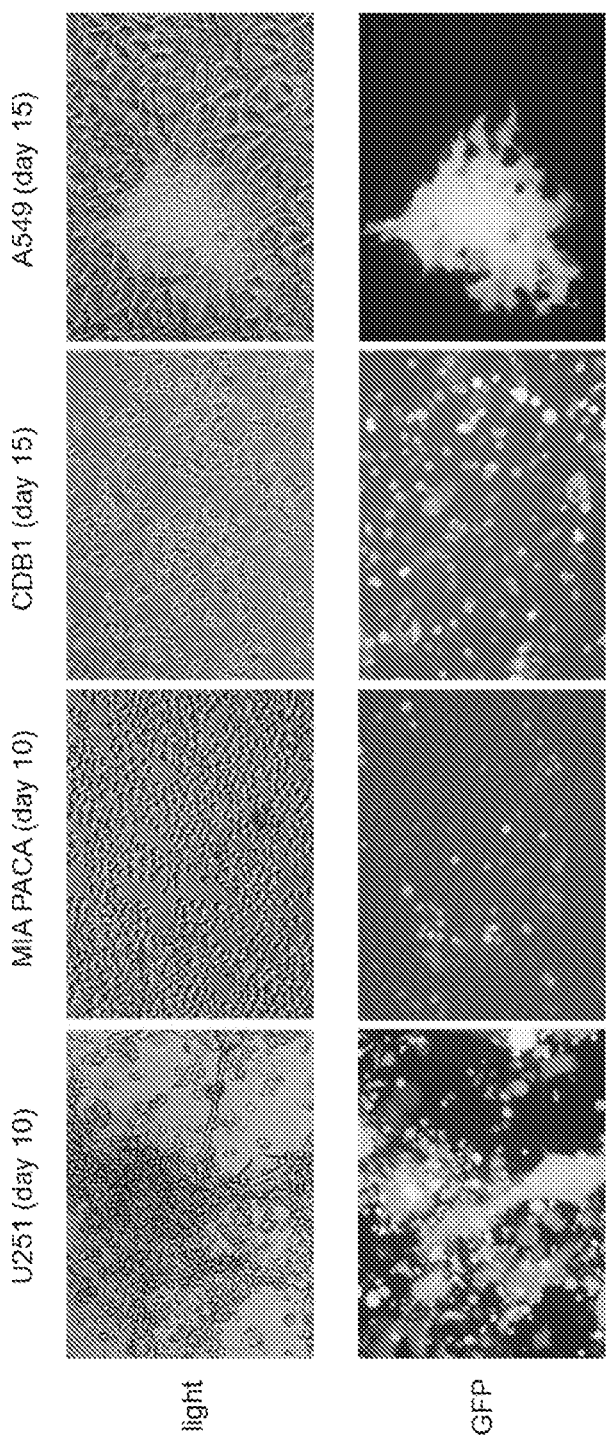
FIG. 8 contains light microscopy images of different cancer cell lines infected with PAN1/2c-GFP. Number of days next to the name of each cell line indicates what day post infection the images were taken.
Figure 9A:
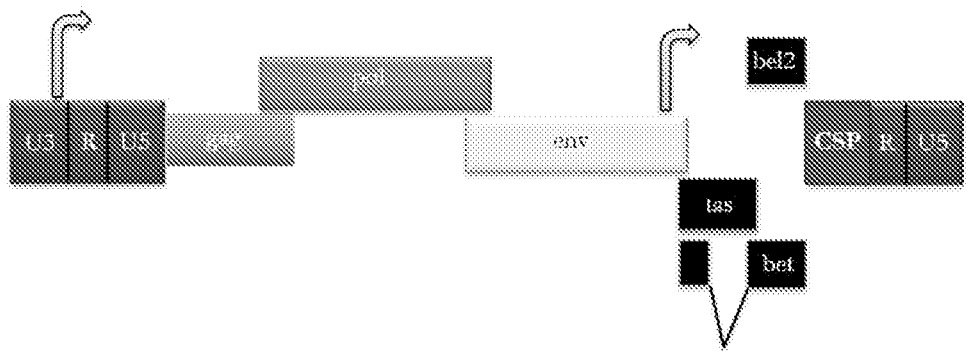
FIGS. 9A and 9B contain exemplary structures of cancer-targeted SFVcpz genomes.
Figure 9B:
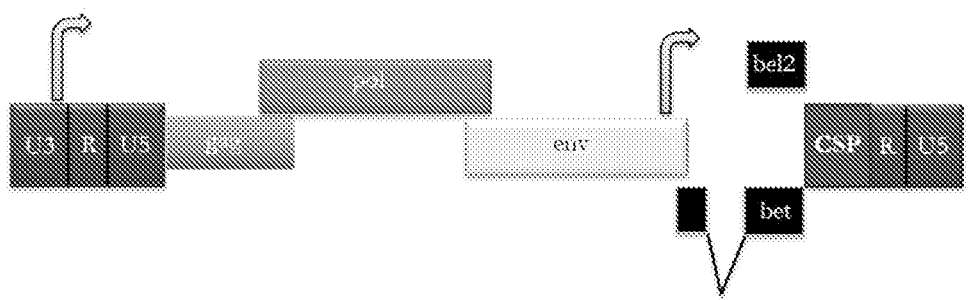
Figure 10A:
FIGS. 10A and 10B contain exemplary structures of cancer-targeted SFVcpz genomes.
Figure 10B:
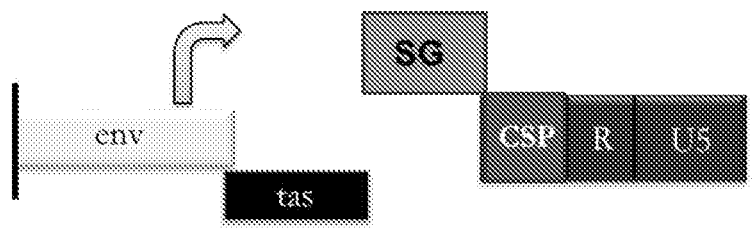

In some cases, a transgene can be a nucleotide sequence encoding another useful polypeptide. Examples of other useful polypeptides include, without limitation, targeting polypeptides (e.g., ligands (e.g., natural ligands and artificial ligands) for cell surface receptors such as cytokines and hormones, single chain antibodies (e.g., targeting cancer antigens such as HER2, CA125, CD19, CD30, CD33, CD123, FLT3, BCMA, CEA, melan-A antigen, and PSA), and other viral envelopes), transport polypeptides (e.g., nuclear localization sequences (NLSs), mitochondorion targeting sequences, and lysosome targeting sequences), therapeutic polypeptides (e.g., immunomodulatory factors such as chemokines and cytokines, antibodies such as antibodies blocking immune checkpoint molecules (e.g., PD-1, PDL-1, and CTLA-4), genome editing systems, viral polypeptides, NISs, and gene repair polypeptides), and cytotoxic polypeptides (e.g., suicide polypeptides such as thymidine kinases, inducible Caspase 9 (iCasp9), NISs, viral polypeptides, and nitroreductase). For example, in cases where a recombinant FV has a deletion of all or part of the bel2 nucleic acid, the bel2 nucleic acid can be replaced with a transgene (e.g., a nucleotide sequence encoding GFP; see, e.g., FIG. 2C). For example, in cases where a recombinant FV has a deletion of nucleic acid the bel2 nucleic acid, the bel2 nucleic acid can be replaced with a transgene (e.g., a nucleotide sequence encoding a suicide polypeptide; see, e.g., FIGS. 10A and 10B). For example, in cases where a recombinant FV has a deletion of nucleic acid the U3 region of the 3' LTR, the U3 region of the 3' LTR can be replaced with a promoter (e.g., a cancer-specific promoter such as a promoter from a tumor antigen or cancer marker such as cancer/testis (CT) antigens (e.g., NY-ESO1), CEA, melan-A antigen, and PSA, and a promoter from a telomerase reverse transcriptase (TERT) such as a human TERT (hTERT)); see, e.g., FIGS. 9A and 9B.

Also provided herein are expression vectors containing a recombinant FV described herein (e.g., a recombinant FV having oncolytic anti-cancer activity). Expression vectors can carry a recombinant FV described herein into another cell (e.g., a cancer cell), where it can be replicated and/or expressed. An expression vector, also commonly referred to as an expression construct, is typically a plasmid or vector having an enhancer/promoter region controlling expression of a specific nucleotide sequence. When introduced into a cell, the expression vector can use cellular protein synthesis machinery to produce the virus in the cell. In some cases, expression vectors containing recombinant FVs described herein can be viral vectors. For example, an expression vector containing a recombinant FV described herein can be a retroviral vector. In some cases, expression vectors including a recombinant FV described herein also can be designed to allow insertion of one or more transgenes (e.g., at a multi-cloning site). For example, expression vectors including a recombinant FV described herein also can include a nucleotide sequence encoding a detectable label. Examples of detectable labels include, without limitation, fluorophores (e.g., GFP, mCherry, YFP, CFP, and Tomato), enzymes (e.g., luciferase, Cas9, Cre recombinase, restriction enzymes, convertases, thymidine kinases, and NISs), and antigens. For example, expression vectors including a recombinant FV described herein can also include a nucleotide sequence encoding another useful peptide. Examples of other useful polypeptides include, without limitation, targeting polypeptides (e.g., ligands (e.g., natural ligands and artificial ligands) for cell surface receptors such as cytokines and hormones, single chain antibodies (e.g., targeting cancer antigens such as HER2), and other viral envelopes), transport polypeptides (e.g., NLSs, mitochondorion targeting sequences, and lysosome targeting sequences), therapeutic polypeptides (e.g., immunomodulatory factors such as chemokines and cytokines, antibodies such as antibodies blocking immune checkpoint molecules (e.g., PD-1, PDL-1, and CTLA-4), genome editing systems, viral polypeptides, NISs, and gene repair polypeptides), and cytotoxic polypeptides (e.g., suicide polypeptides such as thymidine kinases, iCasp9, NISs, viral polypeptides, and nitroreductase).

This document also provides methods and materials for using recombinant FVs described herein (e.g., a recombinant FV having oncolytic anti-cancer activity). In some cases, a recombinant FV provided herein can used for treating a mammal having, or at risk of having, cancer. For example, methods for treating a mammal having, or at risk of having, cancer can include administering one or more recombinant FVs described herein to the mammal. In some cases, methods for treating a mammal having, or at risk of having, cancer can include administering one or more expression vectors that encode a recombinant FV described herein or nucleic acid encoding a recombinant FV described herein to the mammal. In some cases, one or more recombinant FVs described herein can be administered to a mammal to reduce the number of cancer cells in the mammal (e.g., suppress and/or delay tumor growth) and/or to increase survival of the mammal. For example, one or more recombinant FVs described herein can be administered to a mammal to induce syncytia formation of cancer cells within a mammal. In some cases, one or more recombinant FVs described herein can be administered to a mammal to induce vacuolization of a cell of the mammal (e.g., of an infected cell of the mammal). For example, one or more recombinant FVs described herein can be administered to a mammal to induce cell death in a cell of the mammal (e.g., in an infected cell of the mammal).

Any appropriate mammal having, or at risk of having, cancer can be treated as described herein. For example, humans, non-human primates, monkeys, horses, bovine species, porcine species, dogs, cats, mice, and rats having cancer can be treated for cancer as described herein. In some cases, a human having cancer can be treated. In some cases, a mammal (e.g., a human) treated as described herein is not a natural host of a FV used to generate a recombinant FV described herein (e.g., a recombinant FV having oncolytic anti-cancer activity). For example, a human being treated with a recombinant SFV described herein can lack any pre-existing adaptive immunity to SFV.

A mammal having any appropriate type of cancer can be treated as described herein (e.g., treated with one or more recombinant FVs described herein such as a recombinant FV having oncolytic anti-cancer activity). In some cases, a cancer treated as described herein can include one or more solid tumors. In some cases, a cancer treated as described herein can be a blood cancer. Examples of cancers that can be treated as described herein include, without limitation, brain cancers (e.g., glioblastoma), pancreatic cancers (e.g., pancreatic adenocarcinoma), bile duct cancers (e.g., cholangiocarcinoma), lung cancers (e.g., mesothelioma), skin cancers (e.g., melanoma), prostate cancers, breast cancers, ovarian cancers, liver cancers, and colorectal cancers. For example, a cancer treated as described herein can be a glioblastoma. For example, a cancer treated as described herein can be a pancreatic adenocarcinoma. For example, a cancer treated as described herein can be an ovarian cancer.

In some cases, methods described herein also can include identifying a mammal as having cancer. Examples of methods for identifying a mammal as having cancer include, without limitation, physical examination, laboratory tests (e.g., blood and/or urine), biopsy, imaging tests (e.g., X-ray, PET/CT, MRI, and/or ultrasound), nuclear medicine scans (e.g., bone scans), endoscopy, and/or genetic tests. Once identified as having cancer, a mammal can be administered or instructed to self-administer one or more recombinant FVs described herein (e.g., a recombinant FV having oncolytic anti-cancer activity) or a nucleic acid (e.g., an expression vector) encoding a recombinant FV provided herein.

One or more recombinant FVs described herein (e.g., a recombinant FV having oncolytic anti-cancer activity) can be administered by any appropriate route, e.g., intravenous, intramuscular, subcutaneous, oral, intranasal, inhalation, transdermal, and parenteral, to a mammal. In some cases, one or more recombinant FVs described herein can be administered intravenously to a mammal (e.g., a human).

One or more recombinant FVs described herein (e.g., recombinant FVs having oncolytic anti-cancer activity) can be formulated into a composition (e.g., a pharmaceutical composition) for administration to a mammal (e.g., a mammal having, or at risk of having, cancer). For example, one or more recombinant FVs can be formulated into a pharmaceutically acceptable composition for administration to a mammal having, or at risk of having, cancer. In some cases, one or more recombinant FVs can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules. Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some cases, methods described herein also can include administering to a mammal (e.g., a mammal having cancer) one or more additional agents used to treat a cancer. The one or more additional agents used to treat a cancer can include any appropriate cancer treatment. In some cases, a cancer treatment can include surgery. In some cases, a cancer treatment can include radiation therapy. In some cases, a cancer treatment can include administration of a pharmacotherapy such as a chemotherapy, hormone therapy, targeted therapy, and/or cytotoxic therapy. For example, a mammal having cancer can be administered one or more recombinant FVs described herein (e.g., recombinant FVs having oncolytic anti-cancer activity) and administered one or more additional agents used to treat a cancer. In cases where a mammal having cancer is treated with one or more recombinant FVs described herein and is treated with one or more additional agents used to treat a cancer, the additional agents used to treat a cancer can be administered at the same time or independently. For example, one or more recombinant FVs described herein and one or more additional agents used to treat a cancer can be formulated together to form a single composition. In some cases, one or more recombinant FVs described herein can be administered first, and the one or more additional agents used to treat a cancer administered second, or vice versa.

The invention will be further described in the following examples, which do not limit the scope of the invention described in the claims.

EXAMPLES

Example 1: Oncolytic Properties of Simian Foamy Virus (SFV)

Materials and Methods

Infectious Clone Construction

To construct the molecular infectious clone for the chimeric SFVcpz PAN1/2 (SFV type 6/7) virus the genome of the PAN1 virus was amplified from the 5' LTR to the unique restriction site SfiI localized in the pol gene, and the genome of PAN2 from the defective SfiI site (containing a point mutation in the sequence recognized by the restriction enzyme) to the 3' LTR; the total DNA from cells infected with PAN1 and cells infected with PAN2 were used as the templates for the PCR reactions. Both fragments, ~7 kb long each, were cloned into the expression vector pcDNA 3.1 (+), using NheI and NotI restriction sites. In order to recreate the functional SfiI restriction site of the PAN2 genome fragment, mutagenizing primers replacing the mutated A base in the defective SfiI restriction site with the correct G base, and LA Taq polymerase, optimized for the amplification of large products were used. The corrected SfiI site was used to make full length infectious clone, creating the pcDNA3.1-PAN1/2c plasmid. To construct the molecular infectious clone for PAN1, the genome of the virus from 5' LTR to the unique restriction site SfiI, and from the SfiI site to 3' LTR were amplified. Both fragments, ~7 kb long each, were cloned into the expression vector pcDNA 3.1 (+), using NheI and NotI restriction sites. The SfiI site was used to make full length infectious clone, creating the pcDNA3.1-PAN1 infectious clone.

Generation of the GFP-Encoding Virus

To create a GFP-encoding virus, a segment of the PAN1/2 genome from the AflII restriction site in the tas gene to the 3' end of the genome (NotI restriction site) was synthesized, where a portion of the bel2 open reading frame (ORF) (from the 3' end of the tas gene to the Poly Purine Tract) was replaced with the gene encoding GFP. The tas and gfp ORFs were separated by a self-cleaving T2A sequence, enabling the expression of the gfp gene. The synthesized segment was then inserted into the pcDNA3.1-PAN1/2c plasmid using the AflII and NotI restriction sites.

Virus Production

To rescue the constructed viruses, the infectious clones were transfected into 293T cells. After two days BHK-21 cells were added to the culture. Two days later (the 4$^{th}$ day post transfection) the co-cultured cells were passaged. Subsequently, the cells were passaged every 3 days until the infected BHK-21 cells started forming fusions. Then, the cells were transferred into a T-75 flask with fresh, uninfected BHK-21 cells and cultured until large numbers of syncytia appeared. The intracellular viral particles were then released from the cells by 2 cycles of freezing and thawing. Finally, the virus prep was filtered through a 0.45 µl syringe filter and stored in −80° C.

Titer Determination

To determine the titers of the rescued virus preps, an indicator cell line was constructed with a stably integrated lentivector carrying a mcherry or a gfp gene driven by the PAN1 promoter-enhancer elements from U3 of the 3' LTR. $10^5$ of these indicator cells were then seeded in single wells in 24-well plates and infected with either 10 or 50 µl of unconcentrated virus prep. 48 hours post infection the cells were harvested for a flow cytometry analysis to determine the number of mCherry or GFP positive cells.

Infectivity Assays

To verify what cancer cell lines are susceptible and permissive to infection with the SFVs, $10^4$ A549, Mia Paca, U251, CDB-1, and PANC1 cells were infected at MOI 0.5 with PAN1 (from ATCC), PAN1 rescued from the infectious clone, PAN2 (from ATCC), PAN1/2c, PAN1/2c-GFP, and Prototype Foamy Virus (PFV; from ATCC) as a control. The infected cells were passaged every 3-5 days until they were killed by the viral infection.

Western Blot and Indirect Fluorescence Assay Analysis

To detect cells infected with the SFVs, sera from SFV-positive baboons were used. For western blot analyses, the protein lysates from SFV-infected cells were stained with a primate serum and a secondary, anti-monkey, horseradish peroxidase-conjugated antibody. For indirect fluorescence assays, fixed cells were stained with the primate serum and a secondary, anti-monkey, FITC-conjugated antibody. Fluorescence was visualized with a fluorescent microscope.

Results

Two strains of SFVcpz were used: PAN1 and PAN2 (FIG. 1). Infectious clones were generated for PAN1 and for a chimeric virus between PAN1 and PAN2 viruses as described in the material and methods (FIG. 2). The chimeric virus was further modified by replacing a part of the bel2 orf with a gene encoding GFP. The viruses were rescued and the production of viral particles was confirmed by infecting A549 and BHK-21 cells with a sample of the media in which the virus-producer cells were cultured, containing SFV particles. 4 days later the cells were either fixed (for indirect fluorescence assay) or lysed (for western blot) and treated with baboon sera no. 2 or 4. Then stained with secondary antibody conjugated either with horseradish peroxidase or FITC (FIG. 3).

Indicator BHK-21 cell lines with a reporter gene (mCherry or GFP) were created with a lentiviral vector to titrate the SFV viruses. BHK-21 cells (FIG. 4) and indicator BHK-21-U3-mCherry (FIG. 5) were infected either with 50 μl of PAN1/2c or 50 μl of PAN1/2c-GFP and imaged at day 2 post infection. When infected with PAN1/2c, regular BHK-21 cells showed no mCherry or GFP expression (FIG. 4). GFP expression was observed only when infected with the cells were infected with PAN1/2c-GFP (FIG. 4). Indicator BHK-21-U3-mCherry infected with PAN1/2c showed strong mCherry signal, similarly to cells infected with PAN1/2c-GFP, in which the red signal colocalized with the green signal (FIG. 5). All viruses rescued from the infectious clones and viruses obtained from ATCC were titrated using that cell line (FIG. 6). PAN2 and PAN1/2c showed the highest titers among all the viruses. Insertion of the GFP gene into the backbone of PAN1/2c resulted with an approximately 50 fold decrease in titers.

Several different cancer cell lines were infected with PAN1 wt (from ATCC), PAN1 clone (rescued from the infectious clone), PAN2 wt (from ATCC), PAN1/2c, and PFV to compare the cytopathic effects of these viruses and determine permissivity of these cell lines for SFV (FIG. 7). U251 (glioblastoma) and Mia Paca (pancreatic adenocarcinoma) cells turned out to be the most permissive cell lines (A549 the least permissive but still susceptible to infection with the SFVs), whereas PAN1/2c showed the highest cytotoxicity out of all the SFVcpzs used in the study (FIG. 7). Images were taken at day 9 post infection.

These cancer cell lines were also infected with the PAN1/2c-GFP virus, to determine virus' ability to spread in these cell lines in the absence of the Bet protein, which was replaced by GFP (FIG. 8). The virus efficiently spreads in these cell lines. The spread is, however, slower than that of the original virus.

Example 2: Cancer-Specific SFVcpz

Cancer-targeted SFVcpz are engineered by replacing the viral promoter with a cancer-specific promoter. For example, the U3 region of the 3' LTR is replaced with a cancer-specific promoter as shown in FIG. 9A. In some cases, the nucleic acid encoding a tas polypeptide is also deleted as shown in FIG. 9B.

Replacing U3 of the 3' LTR with a cancer-specific promoter minimizes non-specific SFV infection in non-cancer cells.

Specificity of the cancer-specific promoter in vitro by infecting relevant cells (e.g., human cancer cell lines and primary human cancer cells) and non-relevant cells (e.g., non-cancer cells).

In vivo analyses include IV injection and biodistribution analyses between promoter-targeted and wildtype SFVcpz.

Example 3: Armed SFVcpz

Armed SFVcpz are engineered by replacing the viral promoter with a cancer-specific promoter. For example, the nucleic acid encoding a bel2 polypeptide is replaced with a transgene encoding a suicide polypeptide as shown in FIG. 10. In addition, in some cases, the 3' LTR is replaced with a cancer-specific promoter as shown in FIG. 10B.

Arming SFV with a transgene encoding a suicide polypeptide gene enhances tumoricidal effects of the SFV.

Replacing U3 of the 3' LTR with a cancer-specific promoter may minimize unspecific SFV infection in non-cancer cells in vivo.

Example 4: Replication Competent Simian Foamy Virus as an Oncolytic Virotherapy Platform

Materials and Methods

Growth Curves

Multistep growth curve—In a 6-well plate, $1*10^5$ BHK-21-U3-mCherry cells per well were seeded. 3 hours later, the cells were infected with indicated Foamy Viruses at MOI=0.01. Every other day the cells were collected for a Flow Cytometry analysis of mCherry (or GFP) positive cells. On day 4 and day 8 the cells were passed at the 1:5 ratio. The results are plotted as an increase of the percentage of mCherry (or GFP) positive cells over time. The experiment was done in triplicates. On day 8 of the experiment the supernatants of the infected cells were collected, filtered through a 0.45 m filter and the titers of the progeny virions were measured using the indicator BHK-21-U3-mCherry cells. For the cell-associated virus titer, the progeny viruses were released by 2 cycles of freezing and thawing, the cell debris was concentrated by low-speed centrifugation and the supernatant was filtered through a 0.45 m filter. The viral titers in the filtered supernatants were measured using indicator BHK-21-U3-mCherry cells.

One step growth curve—In a 48-well plate, $5*10^4$ BHK-U3-mCherry cells per well were seeded. 3 hours later the cells were infected with PAN1/2 or PAN1/2-GFP at MOI=3. The supernatants were sampled (100 μl) 12, 24, 36, 48, 54, 60, 66, 72, 78, 84, 90, 96, 102, 108, 114, 120 hours post infection and the FV titers in those supernatants were measured using BHK-21-U3-mCherry cells. The experiment was done in duplicates.

Engineering of U251-U3-mCherry-Luciferase Cell Line

U251 cells were transduced with a lentiviral vector encoding the fluorophore mCherry driven by the SFV U3 promoter and a constitutively expressed puromycin resistance cassette. After selection with puromycin, the surviving cells were grown and transduced with a second lentiviral vector, encoding luciferase driven by the SFV U3 promoter and a constitutively expressed neomycin resistance cassette. The transduced cells were selected using neomycin (G418).

In Vitro Luciferase Assay $2*10^4$ U251-U3-mCherry-luciferase cells, U251-U3-mCherry-SFFV-luciferase cells (constitutively express luciferase from the spleen focus forming virus (SFFV) promoter) or wildtype U251 cells were seeded per well of a flat, transparent bottom, black 96-well plate. The cells were infected with PAN1/2 at MOIs 0, 0.2, 1 and 5. On day 3 and 4 post infection, the media was aspirated off from each well, a 20 mg/ml stock of luciferase was diluted 100 fold in PBS and 100 μl of the diluted substrate was added to each well. Bioluminescence was then measured with Tecan Infinite M200 Pro and the results are shown as Relative Light Units (RLU). The experiment was repeated twice in duplicates. On day 3 and 4, the cells infected at MOI=1 were collected and analyzed with flow cytometry for mCherry expression.

In Vivo Experiments

Six-week old CB-17 SCID mice obtained from the vendor Envigo were injected subcutaneously in the right flank with $5*10^6$ U251-U3-mCherry-luciferase cells. When tumors reached the volume of 0.3-0.5 $cm^3$, they were directly injected with 2 doses of $1*10^6$ IU of PAN1/2 or PFV in 100 μl PBS, or 2 doses of 100 μl PBS, or 4 doses of $5*10^5$ IU of PAN1/2-GFP in 100 μl PBS. The mice were inspected and weighted twice a week. The mice were followed for up to 96 days after the first injection unless they reached end-point conditions based on the tumor size (1.7 $cm^3$) or body scoring condition and were euthanized. Once a week, the mice were anesthetized and imaged with Xenogen IVIS-200 system after an intraperitoneal injection of luciferin (100 μl of 20 mg/ml luciferin stock). A total of 5 mice per group were sacrificed in 3 time points for the analysis of the spread of viruses in the tumor. For these mice, half of their tumors were prepared for flow cytometry analysis by mincing, incubation with a solution containing type III collagenase (100 U/ml) and 3 mM $CaCl_2$) for 2 hours at 37° C. on a rocking platform. Then the samples were passed through a cell strainer, concentrated by low-speed centrifugation and re-suspended in PBS containing 4% PFA. For the other half of the tumor, it was covered in OCT and frozen on dry ice. These fragments were then prepared for immunohistochemistry by, briefly, sectioning, fixing in 4% PFA, incubating overnight at 4° C. with primary antibodies at 1:100 dilution: anti-mCherry (all tumors; chicken, polyclonal, Abcam) and anti-GFP (tumors infected with PAN1/2-GFP; rabbit, polyclonal, Abcam). Then, the sections were stained with anti-chicken and anti-rabbit secondary antibodies conjugated with fluorophores, respectively, Alexa 594 and Alexa 488 (1:2000 dilution). The sections were imaged using Zeiss LSM 510 Confocal Microscope and analyzed with the Zen software.

Engineering of PAN1/2-TK and Testing its Functional Activity In Vitro

The Herpes Simplex Virus Thymidine Kinase (TK) was amplified in a PCR reaction using primers with overhangs containing SacII (forward primer) and AgeI (reverse primer) restriction sites. The forward primer overhang also contained the sequence of the T2A self-cleaving peptide. The pcDNA3.1-PAN1/2-GFP plasmid was digested with SacII and BspEI restriction enzymes, and then ligated with the PCR product described above, digested with SacII and AgeI restriction enzymes. This gave rise to the construct pcDNA3.1-PAN1/2-TK. The expression of TK was validated by Western Blot, using a primary anti-TK rabbit antibody, and a secondary, anti-rabbit HRP-conjugated antibody (Santa Cruz Biotechnology). The rescued virus, PAN1/2-TK, was tested in a Ganciclovir killing assay. $1*10^4$ U251-U3-mCherry or CT-26-U3-mCherry cells were seeded per well of a 96-well plate. Then they were infected either with mock control, PAN1/2-TK or PAN1/2-GFP at MOI=1. 2 days (U251-U3-mCherry cells) or 4 days (CT-26-U3-mCherry cells) later, Ganciclovir (Selleckchem, 20 μM final concentration) or mock control was added to the growth media. The viability of the cells was measured using PrestoBlue Cell Viability Reagent (Invitrogen), accordingly to the protocol provided by the supplier. The fluorescence was read using Tecan Infinite M200 Pro at wavelength 560 nm (excitation) and 590 nm (emission). The results are calculated as percent of the fluorescence of the mock-treated control.

Interferon Induction by FV $1*10^5$ A549 cells were seeded per well of a 24 well plate. The cells were then infected with PAN1 (MOI 1 and 10), Vesicular Stomatitis Virus (MOI 1 and 10, Mengovirus (MOI=10) or mock control. 24 and 48 hours after infection the supernatants were collected and human interferon β ELISA (PBL assay science) was run on the samples. The absorbance for the final result was read with Tecan Infinite M200.

Interferon Sensitivity of FV

Patient-derived xenograft glioblastoma GBM22 cells were obtained from The Mayo Clinic Brain Tumor Patient-Derived Xenograft National Resource. $1*10^5$ GBM22 cells were seeded per well of a 24 well plate. 16 hours later the cells were pretreated with human IFNβ (PBL assay science) at 500 units per milliliter or left untreated. 16 hours later, the media was aspirated off and replaced with fresh media containing Ruxolitinib (Apex Bio, 3 M final concentration) or DMSO mock control. The cells that on the previous day were pretreated with IFNβ were also given 500 U/ml of IFNβ during this step. 48 hours later, the media was aspirated off and replaced with fresh media containing only 3 M Ruxolitinib or DMSO control (no IFNβ). Then, the cells were infected with $3*10^5$ IU of PAN1/2-GFP. Two days later, the cells were transferred to a 6 well plate. 6 days post infection the cells were imaged using a fluorescence microscope, the supernatants of the cells were collected and the virus in the samples was titrated using the indicator BHK-21-U3-mCherry cells.

Results

Growth Dynamics of FV

Figure 11A:
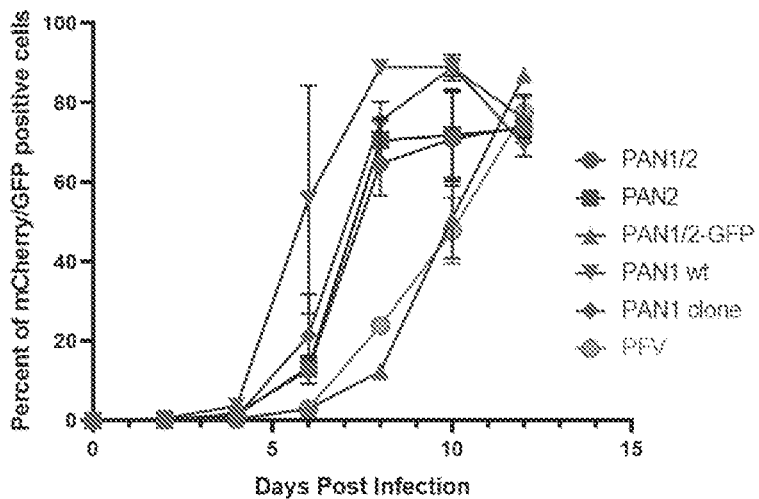
FIGS. 11A-11C show growth dynamics of the Foamy Viruses used in the study.
Figure 11B:
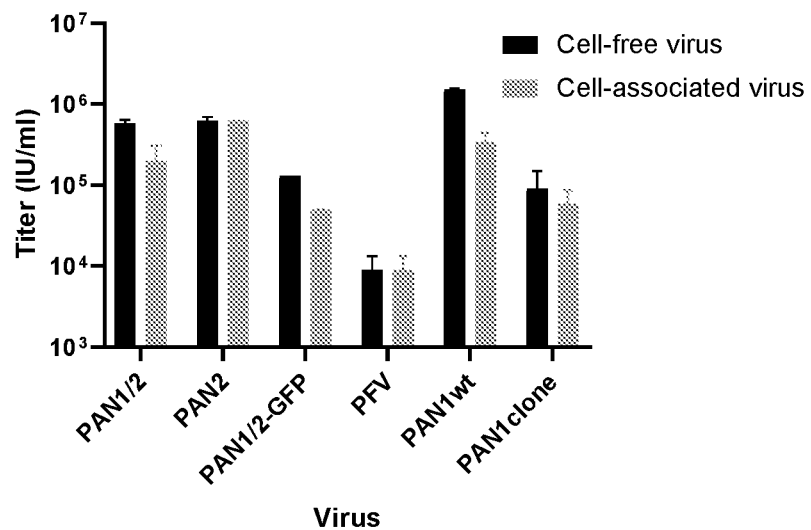

Using the indicator BHK-21-U3-mCherry cells we assessed the replication dynamics of the Foamy Viruses used in the study (FIG. 11). The indicator cells were infected with the FVs at MOI=0.01 and followed the spread of the infection documented as increase in the percentage of mCherry+ cells. FVs spread slowly in the BHK-21-U3-mCherry cells, having infected 80% of cells between day 8 (PAN1 wt) and day 12 (PAN1/2, PAN2, PFV, PAN1/2-GFP) (FIG. 11a). On day 8 post infection, the cell-free fraction of progeny virions of PAN1wt, PAN2 and PAN1/2 reached titers of approximately $10^6$ IU/ml (FIG. 11bB). The titers of the cell free PAN1/2-GFP were approximately 5 fold lower than the titers of the parental PAN1/2 virus and PAN1 clone had similar titers to PAN1/2-GFP (FIG. 11B). PFV reached the lowest titers of all the FVs (~$1*10^4$ IU/ml (FIG. 11)). Interestingly, in case of all these viruses, the cell-associated fraction of progeny viruses is equal or slightly lower than the cell-free fraction (FIG. 11B).

Figure 11C:
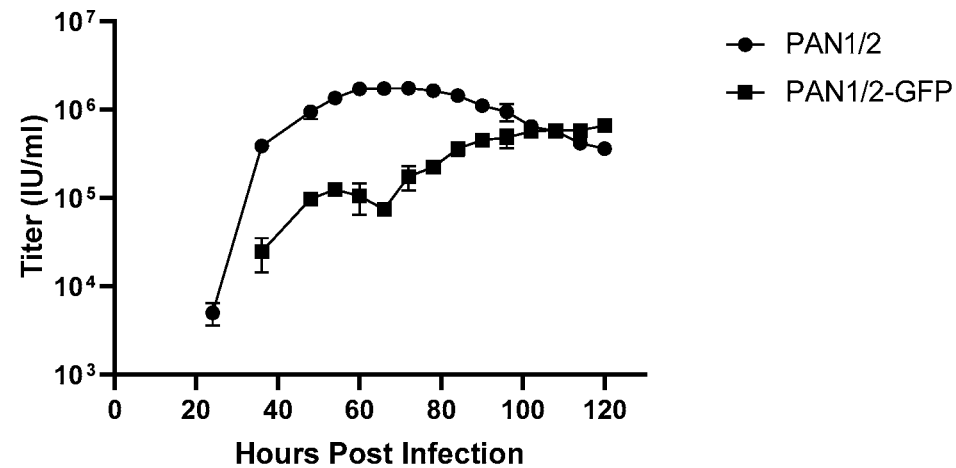

Then, the BHK-21-U3-mCherry cells were infected with PAN1/2 or PAN1/2-GFP at MOI=3 and measured the titers of the progeny virions released into the supernatant over time (FIG. 11C). Newly produced PAN1/2 virus in the supernatant was detectable 36 hours post infection and peaked between 60 and 72 hours post infections, reaching $1.7*10^6$ IU/ml. The release of the PAN1/2-GFP virus particles was slower, reaching titers of $10^5$ IU/ml as late as 54 hours post infection, and peaking at ~$6*10^5$ IU/ml 108 hours post infection. These data indicate that the FVs replicate slowly and need to be cultured for a prolonged period of time to achieve higher titers. The insertion of a transgene (e.g., gfp) resulted in attenuation of the PAN1/2 virus; it replicated slower and its titers were lower than those of the parental virus.

Engineering of a Cancer Cell Line Allowing for Non-Invasive Imaging of FV's Replication In Vivo To test the oncolytic activity of FV and monitor its replication in vivo, the human glioblastoma U251 cell line was engineered to express mCherry and luciferase under the control of the FV promoter and enhancer elements in the U3 of the FV LTR (U251-U3-mCherry-luciferase). Luciferase catalyzes a reaction that produces bioluminescence after the addition of its substrate—Luciferin. Therefore, the FV replication in tumors formed by the U251-U3-mCherry-luciferase cells can be monitored non-invasively and quantitatively using the Xenogen imaging system.

Figure 12D:
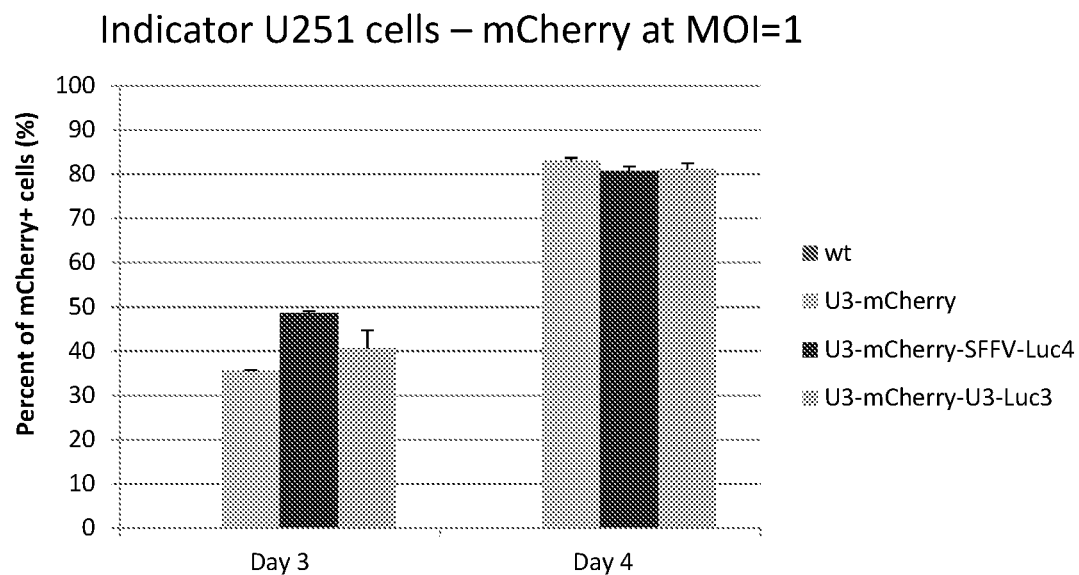
Figure 12E:
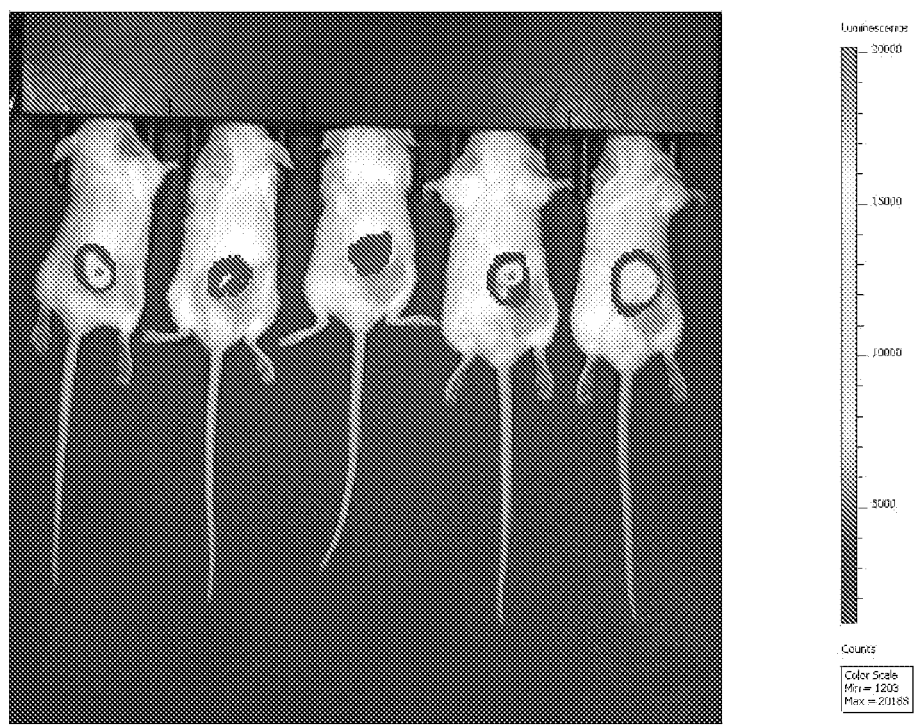

Infection of the U251-U3-mCherry-luciferase cells with PAN1/2 resulted in the expression of the red fluorescence protein mCherry (FIG. 12A, 12D) and luciferase (FIG. 12B, 12C, 12E). The activity of luciferase increased with the MOI and over time, between day 3 and 4 post infection (FIG. 12B, 12D). This correlated with the expression of mCherry, which increased from day 3 to day 4 (FIG. 12D). These data indicate that the magnitude of luciferase activity is strongly dependent on the number of FV-infected cells. Interestingly, the bioluminescence in the infected U251-U3-mCherry-luciferase cells was ~7 fold higher than in U251 cells with constitutively expressed luciferase, driven by the Spleen Focus Forming Virus (SFFV) promoter (FIG. 12C). In vivo, in tumors formed after a subcutaneous injection of U251-U3-mCherry-L in CB-17-SCID mice, PAN1/2 infected cells exhibited bioluminescence after an intraperitoneal injection of luciferin. Thus, the replication of PAN1/2 was visualized in those tumors, as early as 4 days post PAN1/2 injection (FIG. 12E).

Figure 13A:
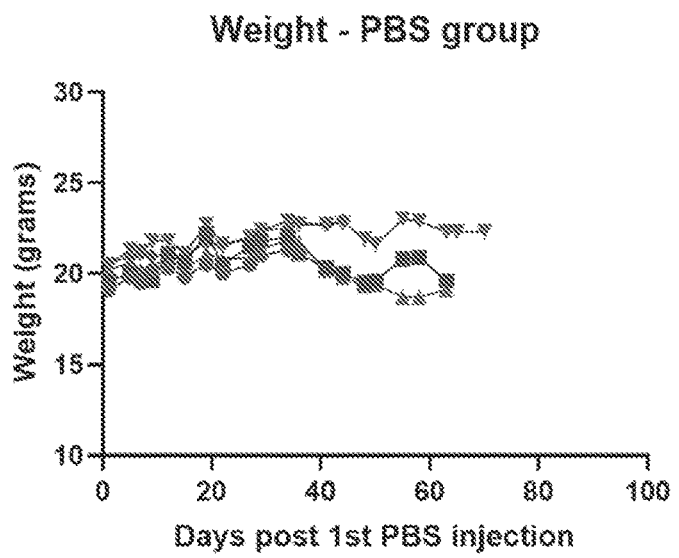
FIGS. 13A-13C show that foamy viruses replicate in tumors in vivo.
Figure 13A:
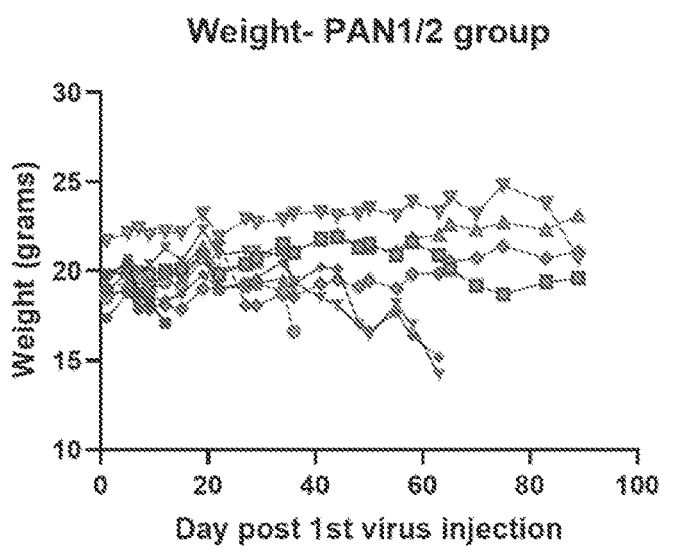
Figure 13A:
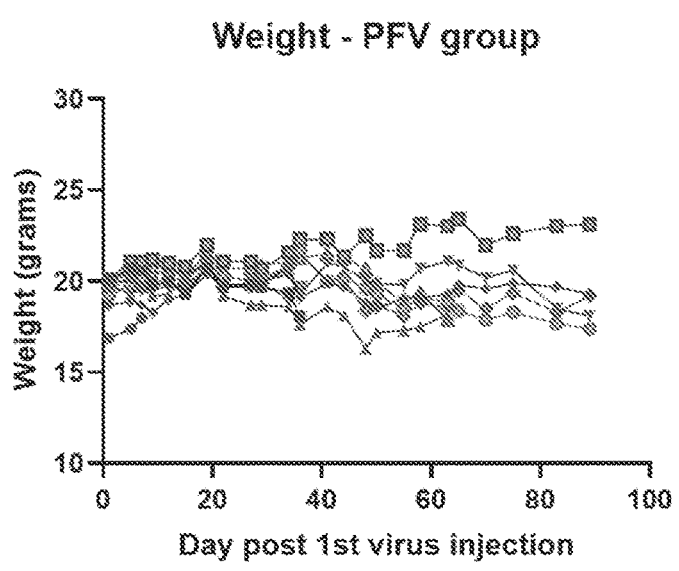
Figure 13B:
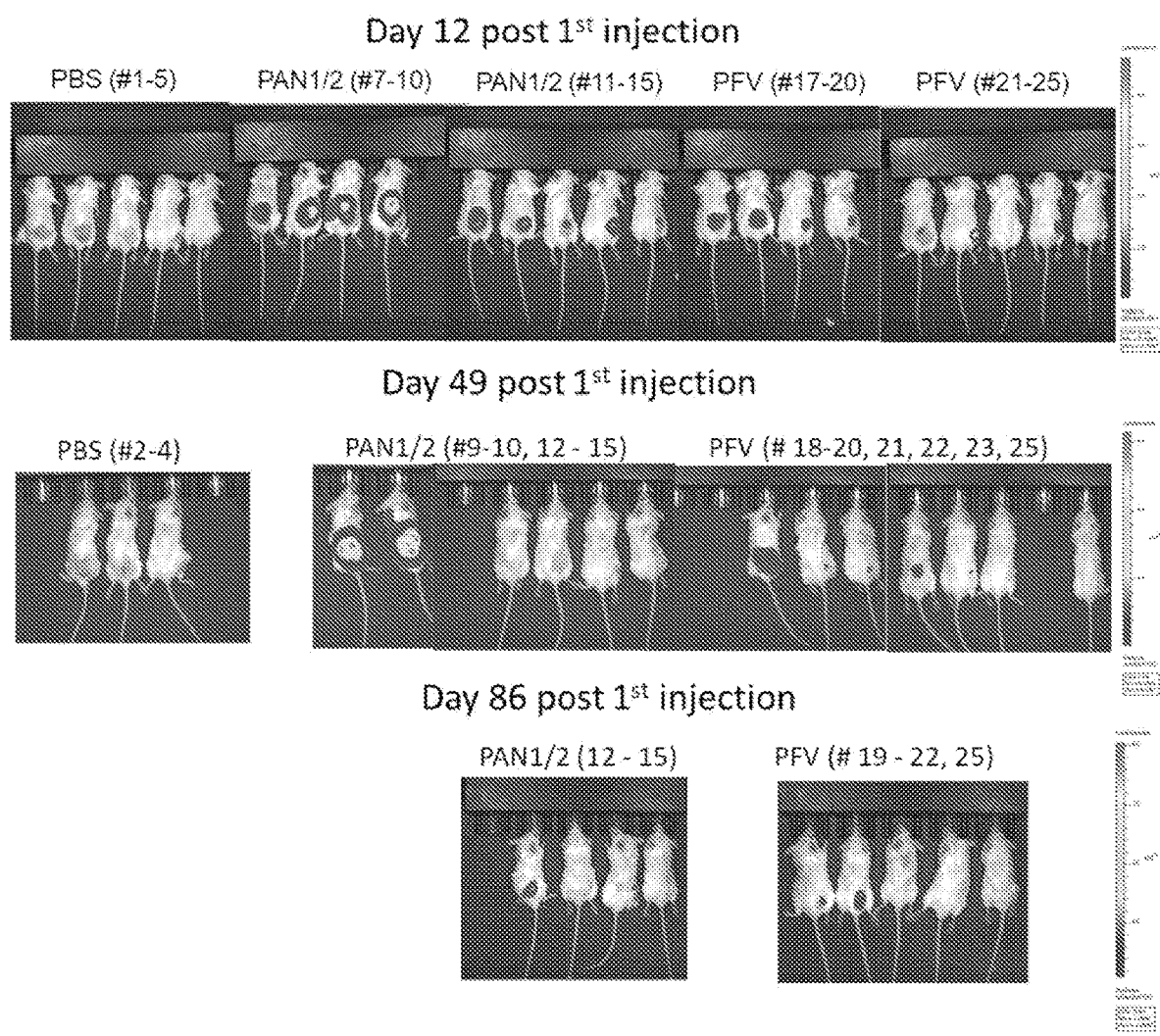
Figure 13C:
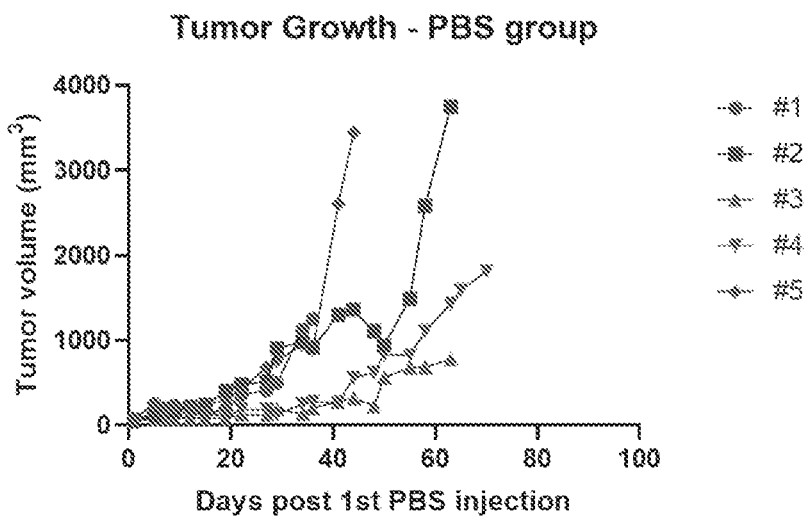
Figure 13C:
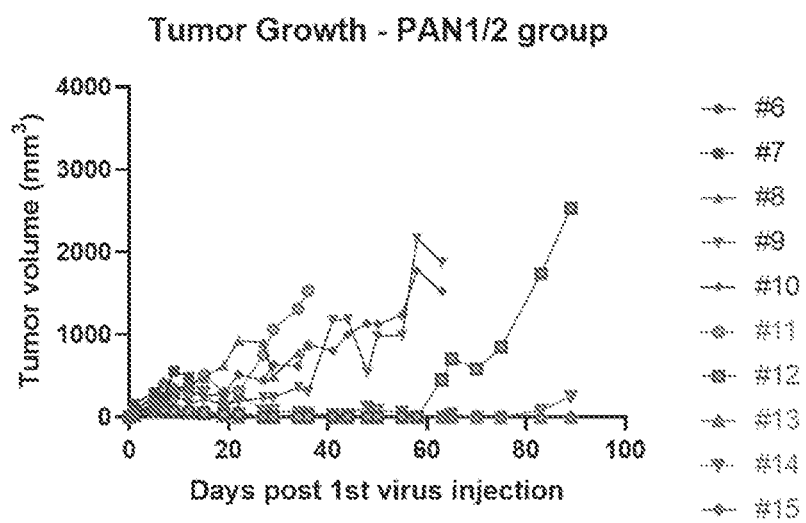
Figure 13C:
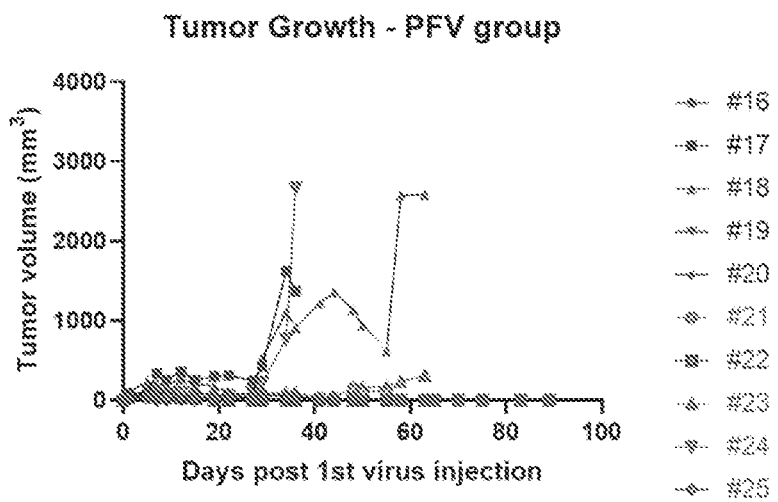

PAN12 Efficiently Replicates and Persists In Vivo in Tumors without Causing Significant Toxicity CB-17 SCID mice were subcutaneously implanted with indicator U251-U3-mCherry-luciferase cells. When tumors were formed, two doses of $1*10^6$ IU of PAN1/2; $1*10^6$ IU of PFV or 100 µl of PBS were injected intratumorally (IT). The viruses did not cause significant toxicity, demonstrated by the healthy weights of the injected mice throughout the experiment (FIG. 13A) (the only cases of substantial weight lost are due to tumor burden). The replication of the FVs in the tumors was monitored weekly via Xenogen imaging (FIG. 13B). Bioluminescence was observed only in the PAN1/2 and PFV-injected mice, not in the PBS-injected mice (FIG. 13B), proving that the system is not leaky and truly allows for the detection of FV replication. Bioluminescence was consistently stronger in the PAN1/2-injected tumors, compared to the PFV-injected tumors, which indicates that PAN1/2 replicates faster than PFV in those tumors. This is consistent with in vitro observations (FIG. 11A). In some cases (PAN1/2-injected mice #12-15 and PFV-injected mice #19-22, #25), the bioluminescence decreased over time (FIG. 13B), what was consistent with the shrinkage of the injected tumors (FIG. 13C). This indicates that SFV replication can result with a direct antitumoral effect. In two cases (PAN1/2-injected mice #9-10) bioluminescence increased over time, as the tumor size increased (FIGS. 13B and 13C). PAN1/2 persisted in the injected tumors and its replication could be detected with the Xenogen technology until the last imaging, on day 86 post $1^{st}$ virus injection. (FIG. 13B). The virus was also recovered from the tumors of the mice sacrificed at the end of the experiment—day 96 post last virus injection (data not shown). The PBS-injected tumors grew faster than FV-injected tumors and all those mice were euthanized due to tumor burden before day 69 post $1^{st}$ PBS injection (FIG. 13C).

Figure 14A:
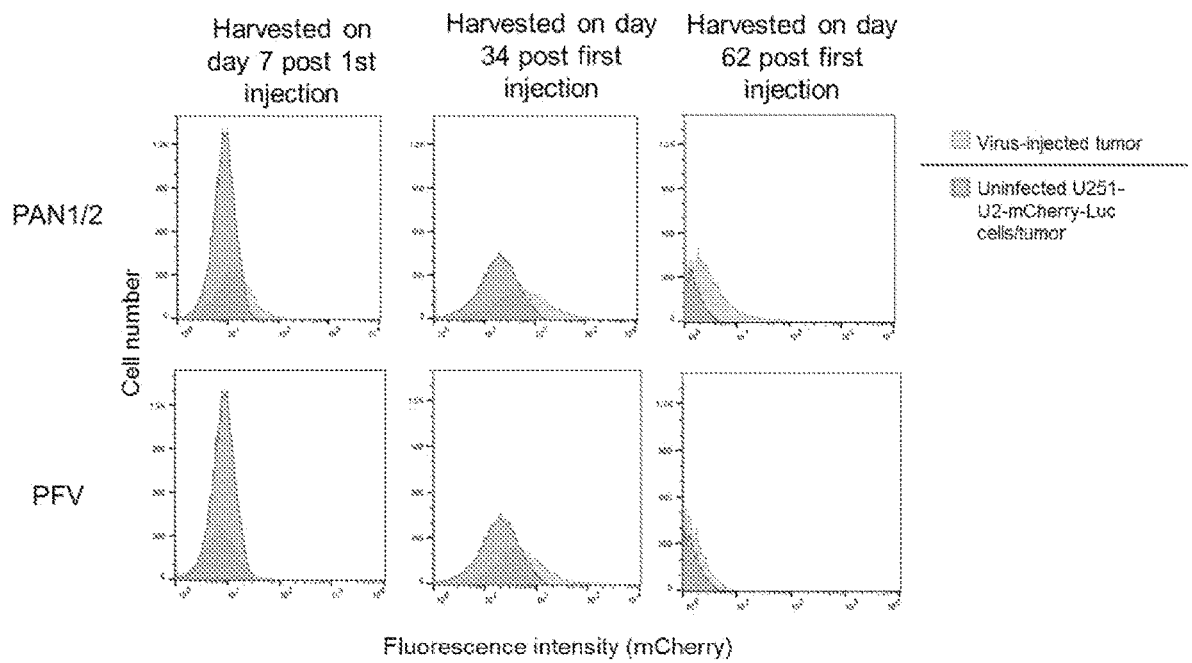
FIGS. 14A and 14B show that FV-injected U251-U3-mCherry-luciferase tumors express mCherry.
Figure 14B:
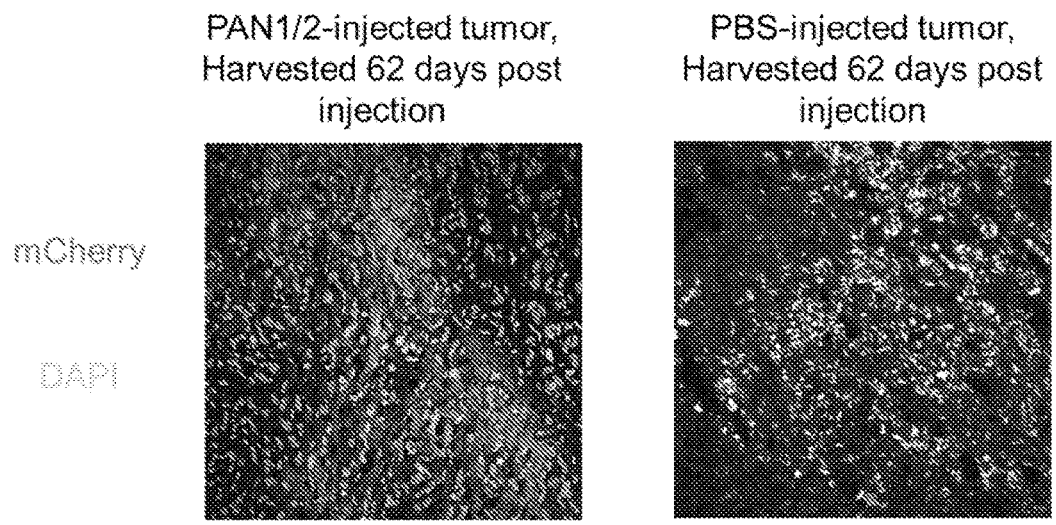

The mice bearing tumors injected with PAN1/2 and PFV were sacrificed at 3 different time points—days 7, 34 and 62 post $1^{st}$ virus injection. Their tumors were analyzed by flow cytometry to determine the percentage of mCherry+ cells (i.e., the percentage of virus-infected cells) (FIG. 14A). On day 7, the percentage of mCherry+ cells was higher in the PAN1/2—than the PFV-injected tumor and it further increased overtime. It also remained higher than at every subsequent time point (FIG. 14A). A PAN1/2-injected tumor and a PBS-injected tumor harvested 62 days post first injection were also sectioned, stained for mCherry and imaged with confocal microscopy (FIG. 14B). mCherry positive cells were easily detected in all sections of the PAN1/2 injected tumor, but not the PBS-injected tumor.

These data indicate that PAN1/2 virus replicates very well in susceptible tumors in vivo, persists in those tumors for a prolonged period of time without causing significant toxicity in the infected mice. As such, the virus can be used for gene delivery in vivo. It may also be superior to PFV due to faster replication and more efficient spread throughout the injected tumor.

Figure 15A:
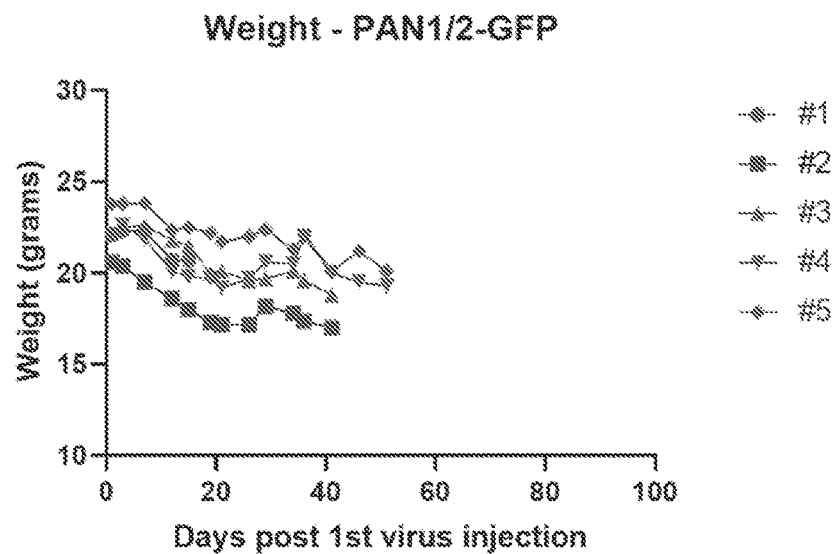
FIGS. 15A-15D show that PAN1/2-GFP delivers a gfp transgene to the indicator U251 tumors and persists in vivo.
Figure 15B:
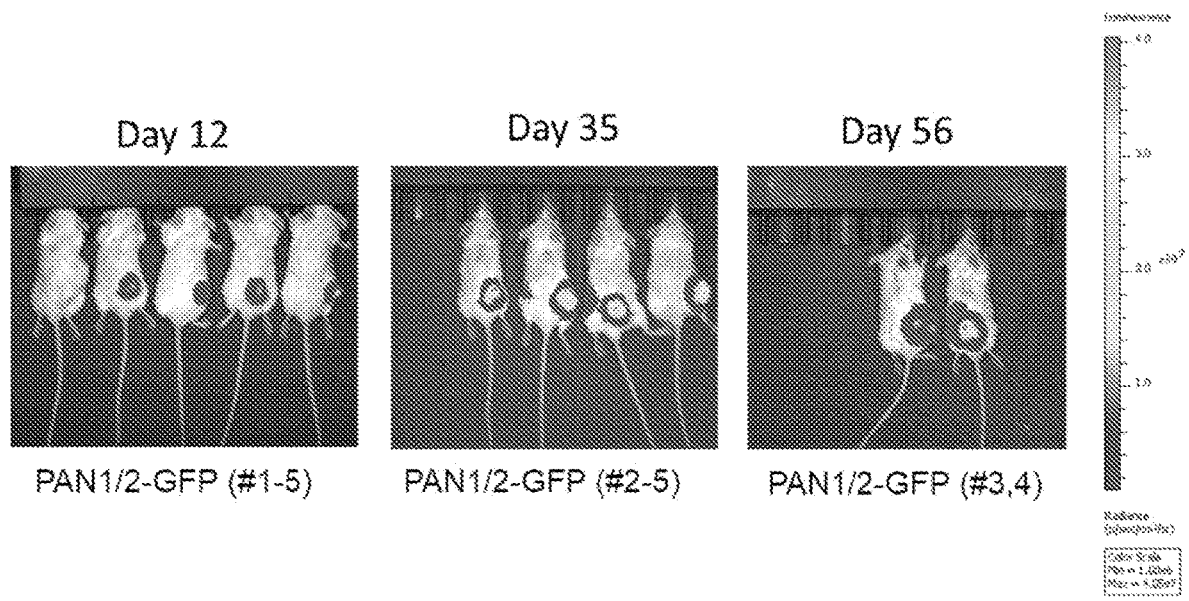
Figure 15C:
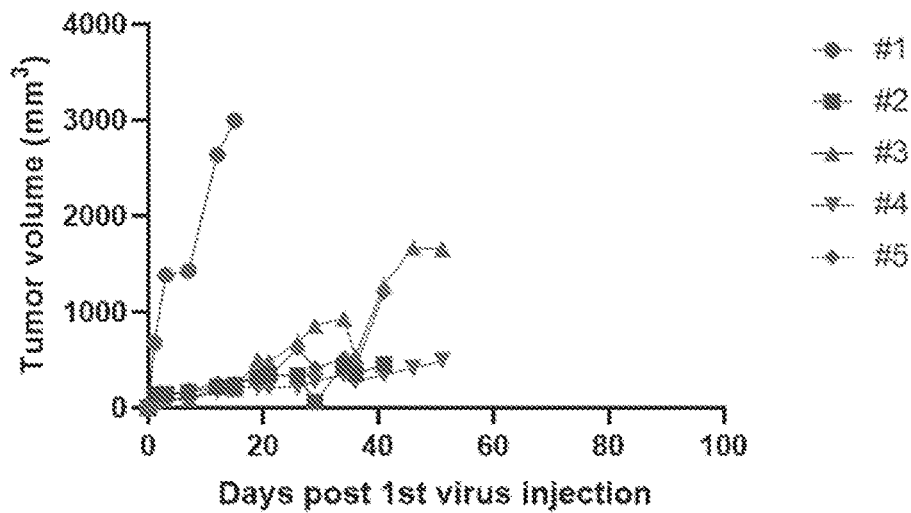
Figure 15D:
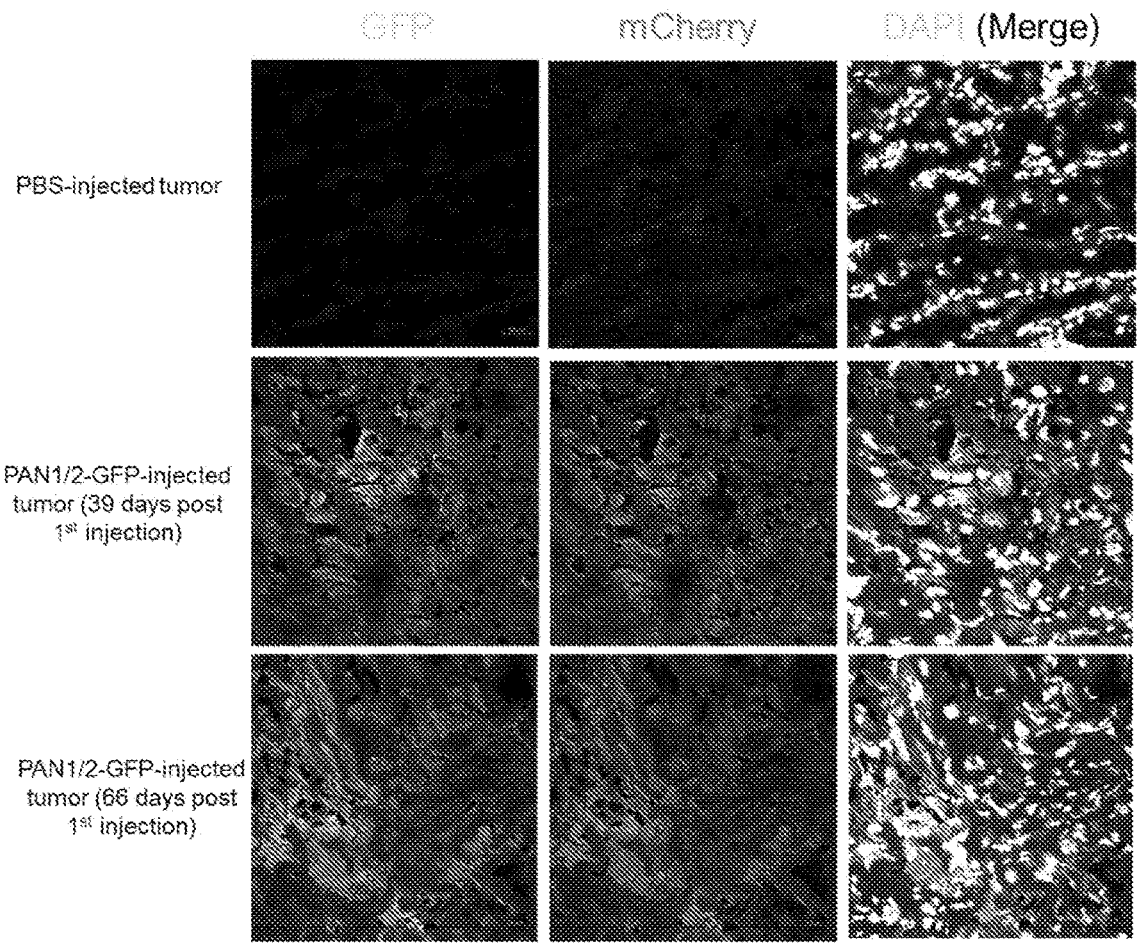

Successful Delivery and Prolonged Expression of the Gfp Transgene by PAN12-GFP in Indicator U251 Tumors To verify whether PAN1/2 can deliver transgenes into tumors in vivo, indicator U251-U3-mCherry-luciferase cells were injected into CB-17 SCID mice and upon tumor formation were intratumorally injected with 4 doses of $5*10^5$ IU of PAN1/2-GFP. The virus was well tolerated by the injected mice, as indicated by their body weights (FIG. 15A). Bioluminescence on day 12 post $1^{st}$ injection (6 post last injection) was detectable for 4 out of 5 mice (the large size of the tumor of mouse #1 could have affected imaging) (FIG. 15B). The bioluminescence became stronger on day 19 and remained strong until the last time the mice were imaged (day 56, FIG. 15B). The replication of the virus did not seem to have affected the tumor growth substantially (FIG. 15C). On days 13, 39 and 66 after the first virus infection mice were sacrificed and their tumors were sectioned, stained for mCherry and GFP and imaged with confocal microscopy (FIG. 15D). All sections of the PAN1/2-GFP-injected tumors harvested on days 39 and 66 were positive for mCherry and GFP and those signals co-localized (FIG. 15D). A control, PBS-injected tumor, was negative for both fluorophores. This demonstrated that PAN1/2 can be used for delivery of transgenes into tumors. As the virus spreads, more tumor cells will express the transgene. In an immune-deficient animal model, the expression of transgenes delivered by the virus is sustained for a prolonged period of time.

Arming of PAN1/2 with a Suicide Gene Herpes

Figure 16A:
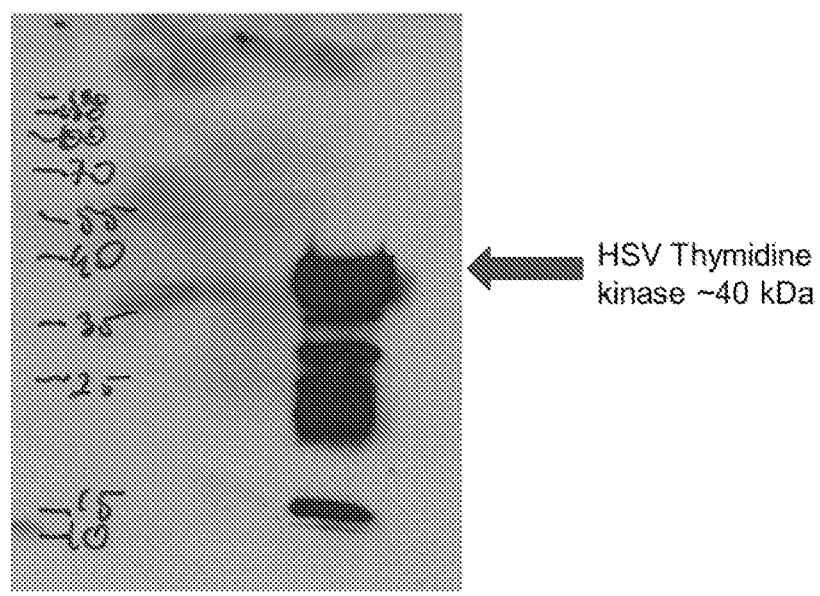
FIGS. 16A-16E show PAN1/2-TK infection results with the expression of TK and an increase in the sensitivity to Ganciclovir of the infected cells.
Figure 16B:
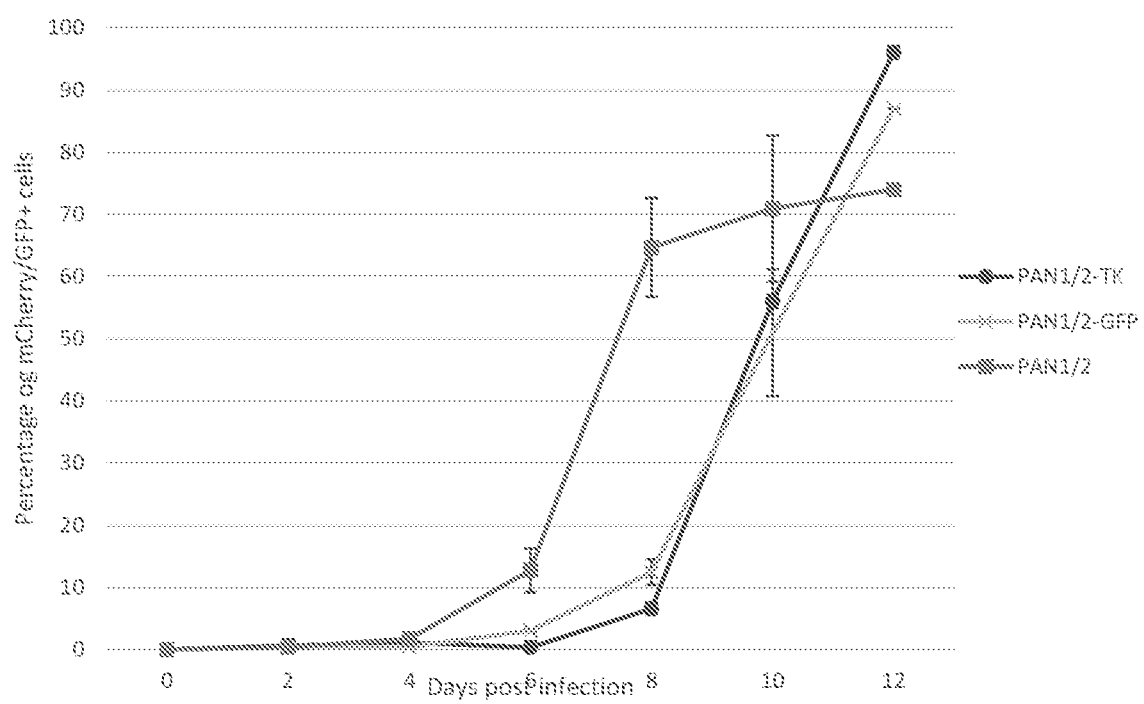
Figure 16C:
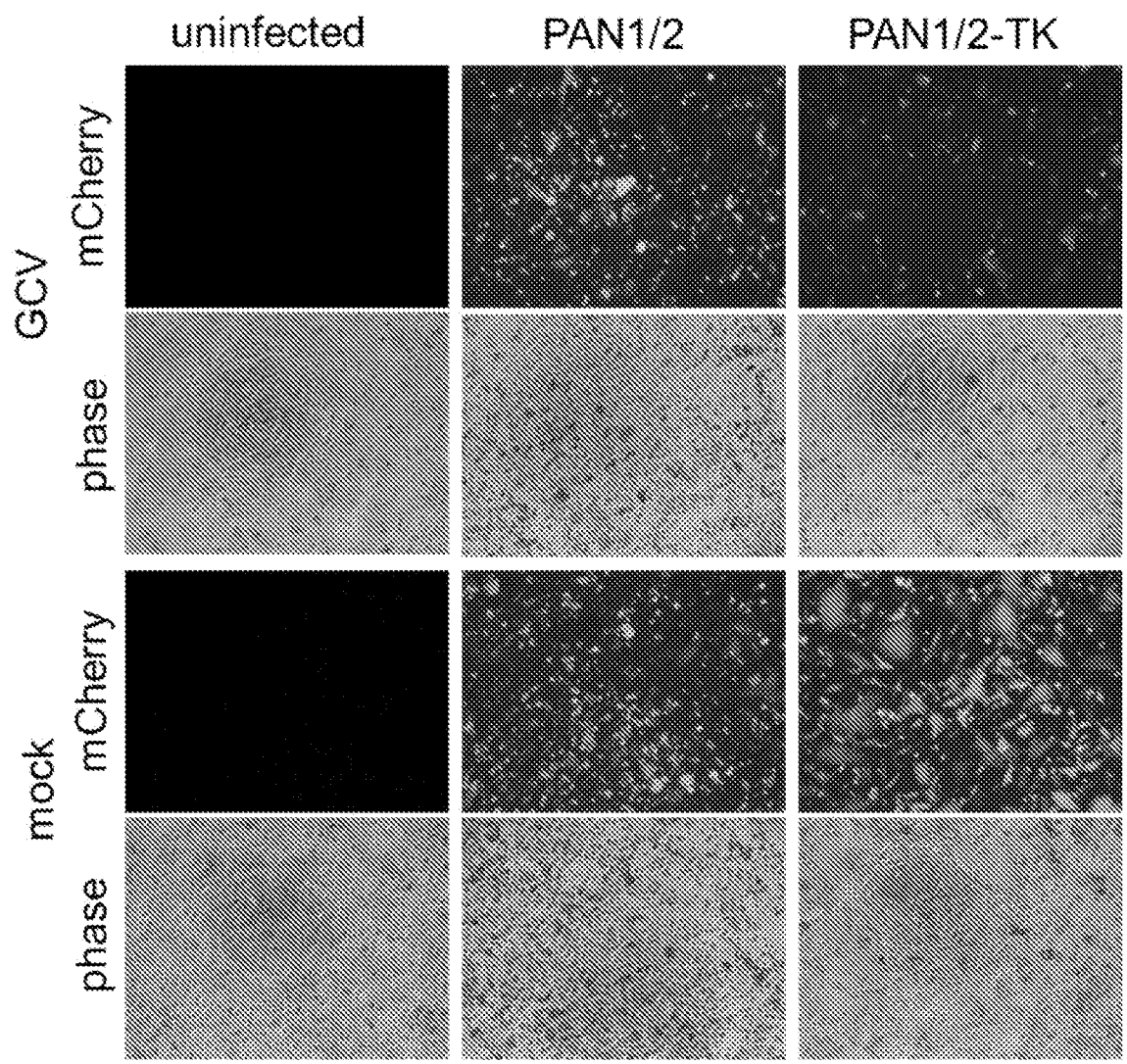
Figure 16D:
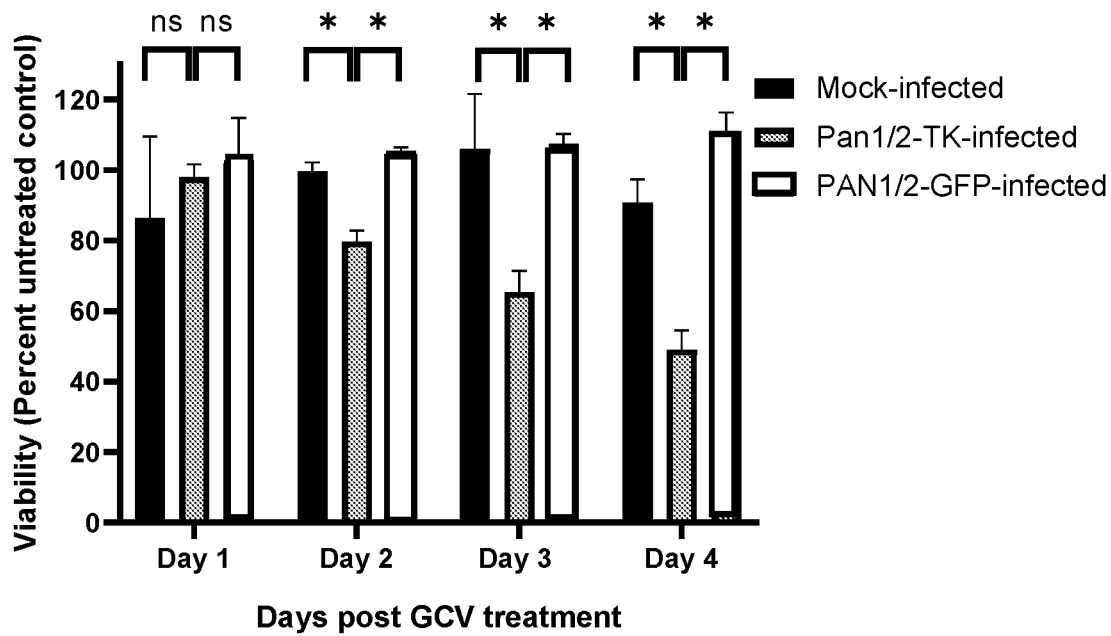
Figure 16E:
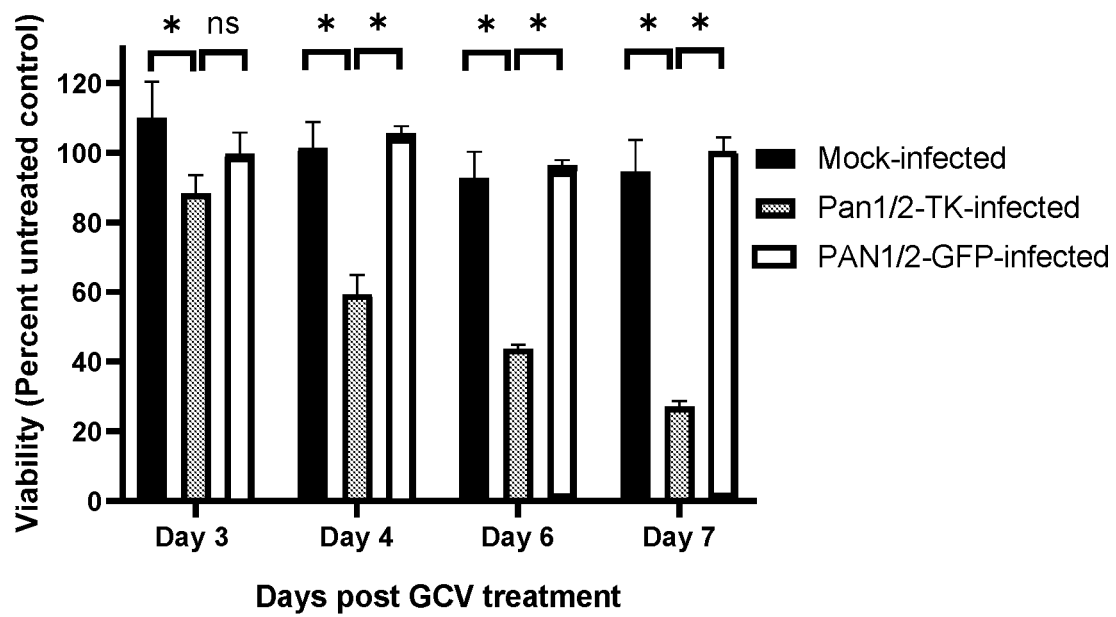

16C). The number of mCherry positive cells was visibly lower in the case of PAN1/2-TK infected and GCV-treated samples than in case of the mock-treated or PAN1/2-GFP-infected samples (FIG. 16C). The viability of the PAN1/2-TK-infected and GCV-treated indicator U251 cells began decreasing significantly 48 hours post the GCV treatment and it continued to decrease over time, when compared to mock-infected or PAN1/2-GFP-infected cells (FIG. 16D). The viability of the PAN1/2-TK-infected indicator CT-26 cells was dropping slower upon GCV treatment, reaching significant decrease compared to the mock infected cells 72 hours post GCV treatment, and compared to PAN1/2-GFP infected cells—96 hours post GCV treatment. On day 7 post GCV treatment, the viability of the PAN1/2-TK infected cells dropped to 26% (FIG. 16E). These data prove that HSV-TK delivered by PAN1/2-TK significantly increases the sensitivity of the infected cells to GCV. PAN1/2, therefore, can be armed with a therapeutic suicide gene to more efficiently induce cell death.

SFV is Sensitive to Exogenous Interferon β, but does not Induce Interferon f Production in Infected Cells.

Figure 17A:
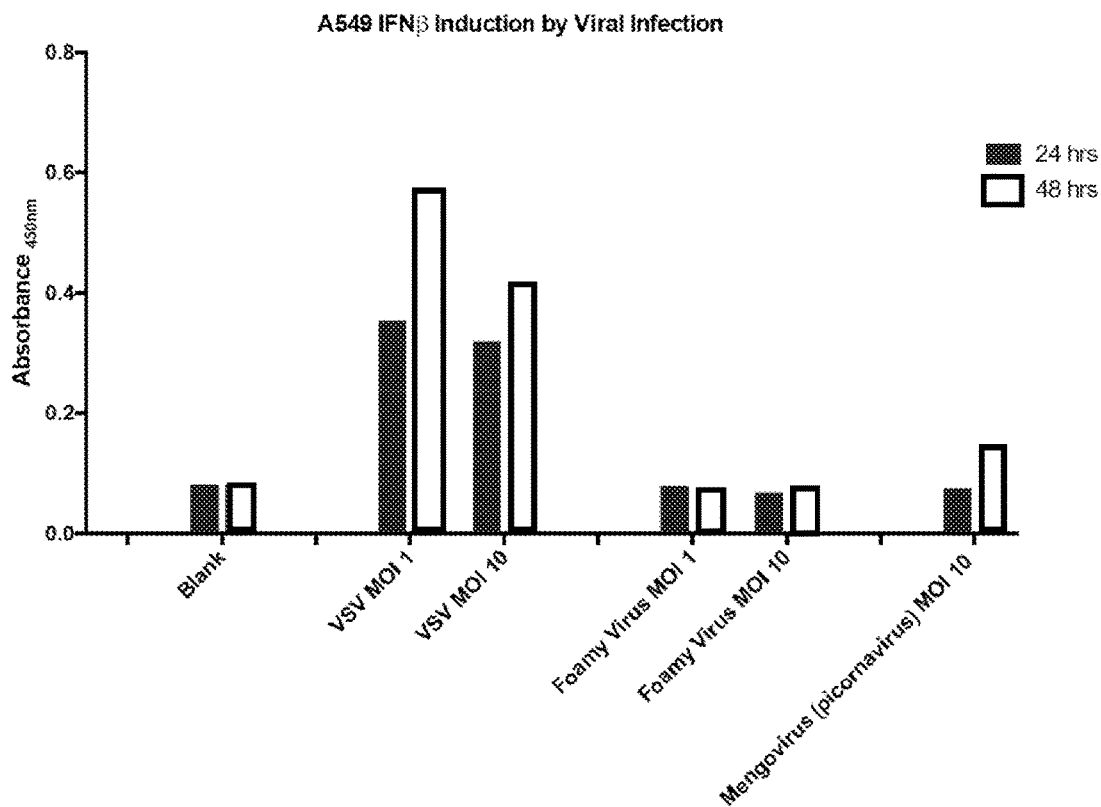
FIGS. 17A-17C show that FVs do not induce Interferon β production but are sensitive to Interferon β-induced antiviral state.

Tumor cells, similarly to normal cells, often can respond to viral infection by producing Interferon β (IFNβ) which induces antiviral state, and some tumors can even produce IFNβ constitutively. This leads to a decrease in the efficacy of oncolytic virotherapy. It was therefore investigated whether SFV induces IFNβ production in infected cancer cell lines and whether it is sensitive to IFNβ. Human lung adenocarcinoma A549, a cell line known to produce IFNβ in response to viral infection, was infected with PAN1 and Vesicular Stomatitis Virus (VSV) at MOI=1 and 10, and also with Mengovirus at MOI=10. The supernatants of the infected cells were collected 24 and 48 hours post infection and human IFNβ ELISA was run on these samples. VSV induced IFNβ production already 24 hours post infection at both MOIs (FIG. 17A). Production of IFNβ by cells infected with Mengovirus was detectable 48 hours post infection (FIG. 17A). Unlike VSV and Mengovirus, PAN1 did not induce IFNβ production at either of the MOIs (FIG. 17A).

Figure 17B:
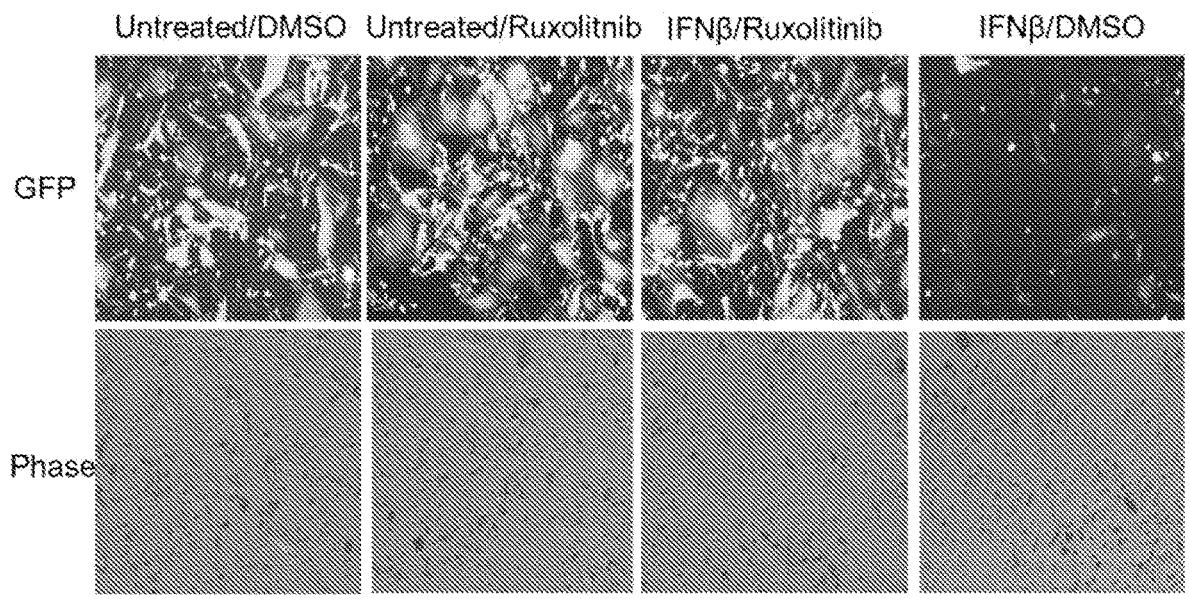
Figure 17C:
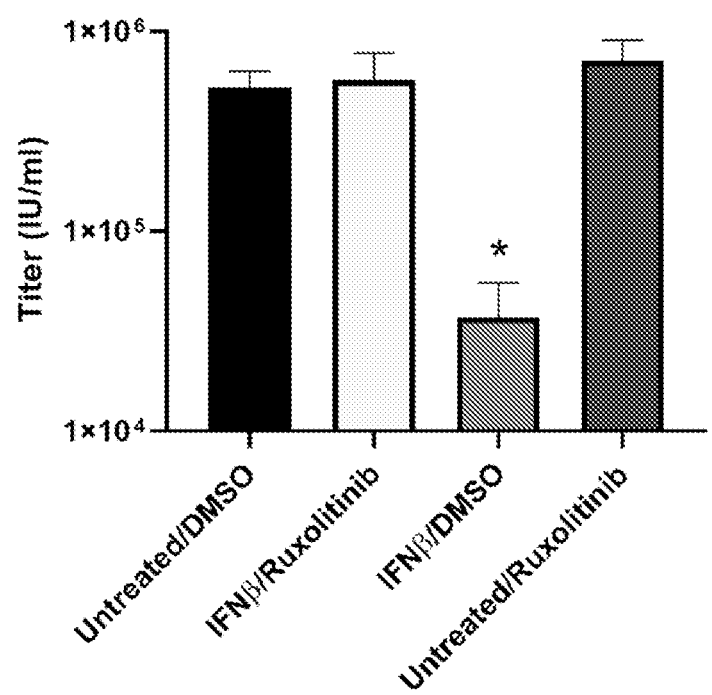

Next, it was verified whether SFV is sensitive to IFNβ and whether a JAK-STAT pathway inhibitor Ruxolitinib can reverse this effect. Patient-derived human glioblastoma line GBM22 was pretreated with exogenous human IFNβ or left untreated. 16 hours later we treated the cells with Ruxolitinib or DMSO control. 48 hours later, the cells were infected with $3*10^5$ IU of PAN1/2-GFP. 6 days post infection, the cells were imaged (FIG. 17B) and the titers of newly produced PAN1/2-GFP virions in the supernatants were measured (FIG. 17C). The cells treated with IFNβ+Ruxolitinib showed level of GFP expression similar to cells not treated with IFNβ and treated with DMSO or Ruxolitinib (FIG. 17*b*). Similarly, the PAN1/2-GFP titers in the supernatants of the cells treated with IFNβ+Ruxolitinib did not significantly differ from the PAN1/2-GFP titers in the supernatants of the cells not treated with IFNβ and treated with DMSO or Ruxolitinib (FIG. 17C). However, the cells treated with DMSO and IFNβ showed significantly lower level of GFP expression than any of the combinations above (FIG. 17B), and the titers of PAN1/2-GFP recovered from their supernatants were ~10 fold lower (FIG. 17C). These data indicate that SFV does not induce IFNβ production in the tested cancer cell lines. SFV is sensitive to the IFNβ-induced antiviral state in primary cells, however, this effect can be reversed by Ruxolitinib, allowing the virus to successfully infect and replicate in those cells.

Example 5: T Cells Expressing CARs (CAR-T Cells)

CAR-T cells are engineered by replacing the viral promoter of a SFV with nucleic acid encoding a CAR and infecting T cells with the SFV expressing the CAR. For example, the nucleic acid encoding a bel2 polypeptide is replaced with a transgene encoding a CAR.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A chimeric simian foamy virus (SFV) comprising:

(a) a first genomic fragment comprising a 5' LTR, a nucleic acid encoding a gag polypeptide, and a 5' portion of a nucleic acid encoding a pol polypeptide of a chimpanzee PAN1 SFV strain;

(b) a second genomic fragment comprising a 3' portion of a nucleic acid encoding a pol polypeptide, a nucleic acid encoding an env polypeptide, a nucleic acid encoding a tas polypeptide, a nucleic acid encoding a bel2 polypeptide, and a 3' LTR of a chimpanzee PAN2 SFV strain, and (c) a transgene.

2. The chimeric SFV of claim 1, wherein said 5' portion of said nucleic acid encoding said pol polypeptide and said 3' portion of said nucleic acid encoding said pol polypeptide are separated by a SfiI restriction site.

3. The chimeric SFV of claim 1, wherein said transgene encodes a receptor.

4. The chimeric SFV of claim 3, wherein said receptor is a chimeric antigen receptor (CAR).

5. The chimeric SFV of claim 4, wherein said CAR can target a cancer antigen.

* * * * *

UNITED STATES PATENT AND TRADEMARK OFFICE
CERTIFICATE OF CORRECTION

PATENT NO. : 12,201,659 B2
APPLICATION NO. : 16/980359
DATED : January 21, 2025
INVENTOR(S) : Yasuhiro Ikeda, Karol M. Budzik and Stephen J. Russell Page 1 of 1

It is certified that error appears in the above-identified patent and that said Letters Patent is hereby corrected as shown below:

On the Title Page

Column 2 (item (56) Other Publications), in Line 44, delete "(SFVepz)" and insert -- (SFVcpz) --.

Signed and Sealed this
Eleventh Day of March, 2025

Coke Morgan Stewart
*Acting Director of the United States Patent and Trademark Office*